(12) United States Patent
Sasaki

(10) Patent No.: US 11,143,664 B2
(45) Date of Patent: Oct. 12, 2021

(54) SAMPLE PROCESSING METHOD AND SAMPLE PROCESSING APPARATUS

(71) Applicant: SYSMEX CORPORATION, Kobe (JP)

(72) Inventor: Yuto Sasaki, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 874 days.

(21) Appl. No.: 15/880,705

(22) Filed: Jan. 26, 2018

(65) Prior Publication Data

US 2018/0217171 A1 Aug. 2, 2018

(30) Foreign Application Priority Data

Jan. 31, 2017 (JP) .............................. JP2017-015799

(51) Int. Cl.
*G01N 1/00* (2006.01)
*G01N 35/00* (2006.01)
(Continued)

(52) U.S. Cl.
CPC ........... *G01N 35/0098* (2013.01); *B03C 1/01* (2013.01); *B03C 1/0332* (2013.01); *B03C 1/288* (2013.01); *B03C 1/30* (2013.01); *G01N 35/1011* (2013.01); *B03C 2201/18* (2013.01); *B03C 2201/26* (2013.01); *C12Q 1/6806* (2013.01); *G01N 2035/1039* (2013.01); *G01N 2035/1053* (2013.01); *G01N 2035/1058* (2013.01)

(58) Field of Classification Search
None
See application file for complete search history.

(56) References Cited

U.S. PATENT DOCUMENTS 6,187,270 B1 * 2/2001 Schmitt .................. B03C 1/288
422/527
2008/0182301 A1 7/2008 Handique et al.
2016/0369263 A1 12/2016 Quan

FOREIGN PATENT DOCUMENTS

JP H09-019292 A 1/1997
JP 2003-42912 A 2/2003
(Continued)

OTHER PUBLICATIONS

An Office Action (JPOA) dated Nov. 10, 2020 in a counterpart Japanese patent application.

*Primary Examiner* — Jyoti Nagpaul
(74) *Attorney, Agent, or Firm* — Metrolex IP Law Group, PLLC

(57) ABSTRACT

A sample processing method may include: removing a liquid component in a container housing a suspension containing a magnetic particle bound with an analyte, while causing magnetic adhesion of the magnetic particle in the container; discharging an elution liquid for releasing the analyte from the magnetic particle from a pipette into the container from which the liquid component has been removed so as to mix the magnetic particle and the elution liquid; moving, after discharging the elution liquid into the container, the pipette relative to and close to an inner wall of the container so as to collect a droplet attached to the inner wall onto an outer surface of the pipette; and moving a tip of the pipette to an accumulation area in which the elution liquid accumulates in the container so as to move the droplet collected on the outer surface of the pipette to the accumulation area.

24 Claims, 27 Drawing Sheets

(51) Int. Cl.
*G01N 35/10* (2006.01)
*B03C 1/01* (2006.01)
*B03C 1/033* (2006.01)
*B03C 1/30* (2006.01)
*B03C 1/28* (2006.01)
*C12Q 1/6806* (2018.01)

(56) References Cited

FOREIGN PATENT DOCUMENTS

| | | |
|---|---|---|
| JP | 2010-533490 A | 10/2010 |
| WO | 2010/005444 A1 | 1/2010 |
| WO | 2015/098509 A1 | 7/2015 |

\* cited by examiner

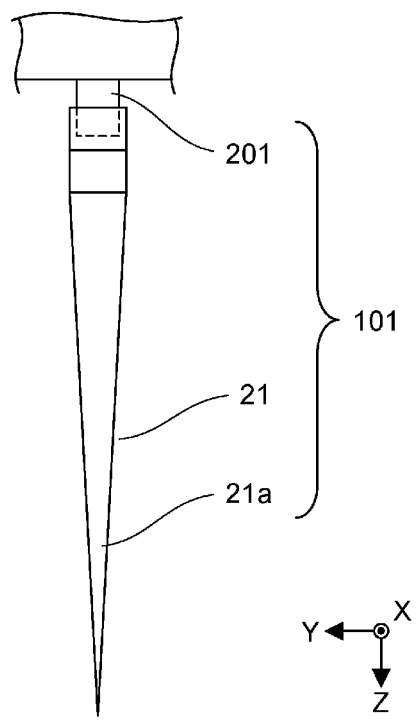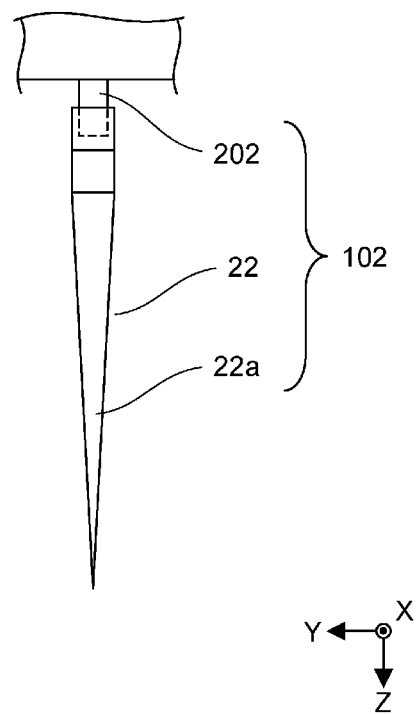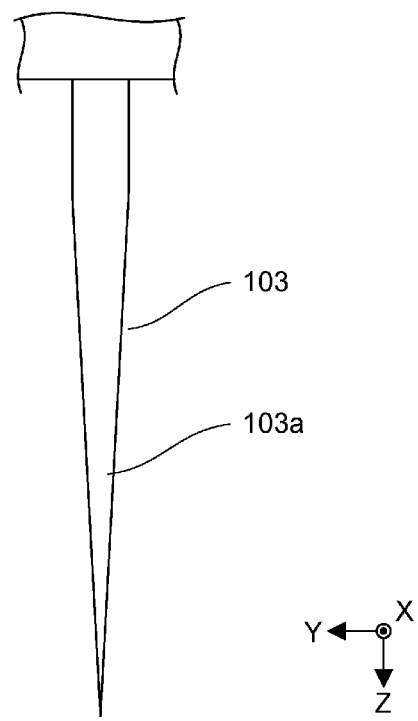
Fig. 3A
Fig. 3B
Fig. 3C

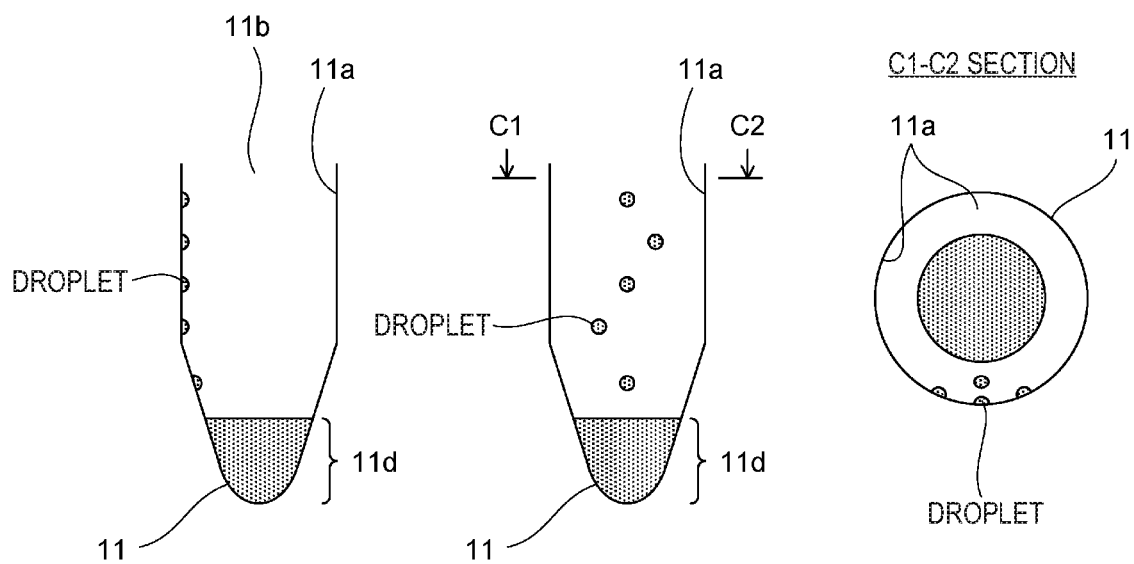
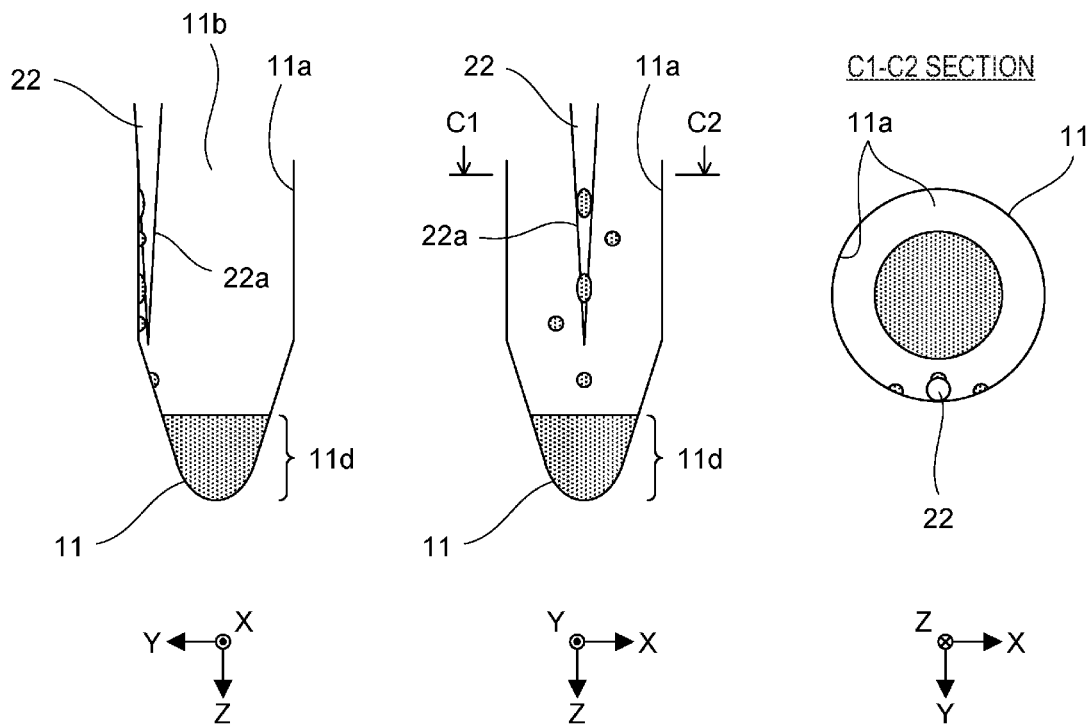
Fig. 5A  Fig. 5B  Fig. 5C
Fig. 5D  Fig. 5E  Fig. 5F

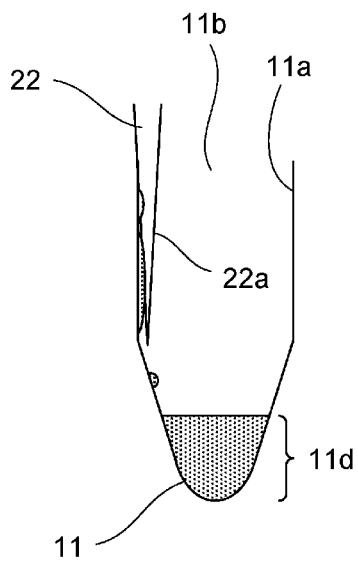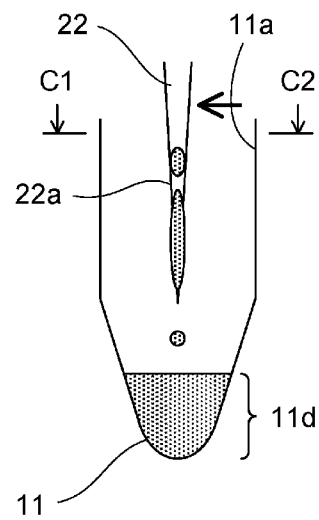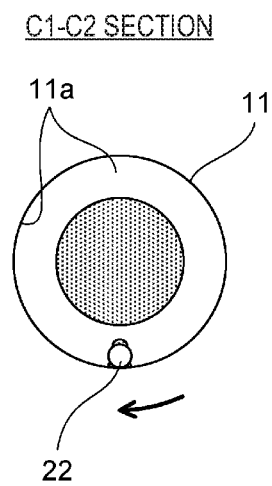
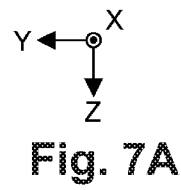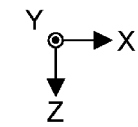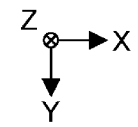
Fig. 7A  Fig. 7B  Fig. 7C
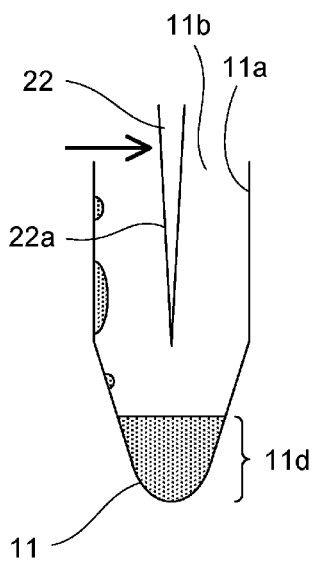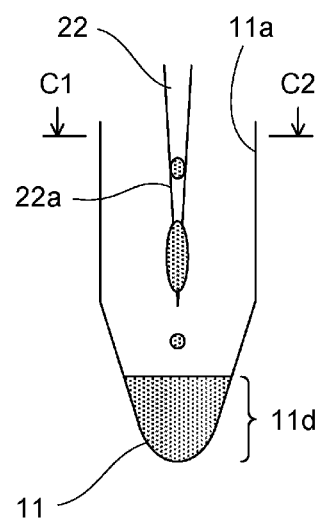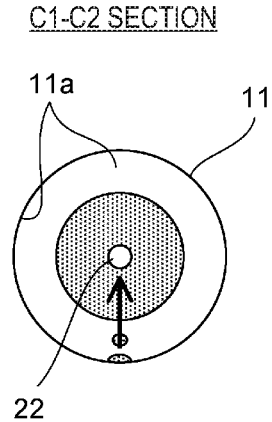
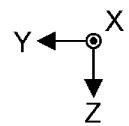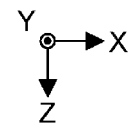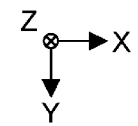
Fig. 7D  Fig. 7E  Fig. 7F

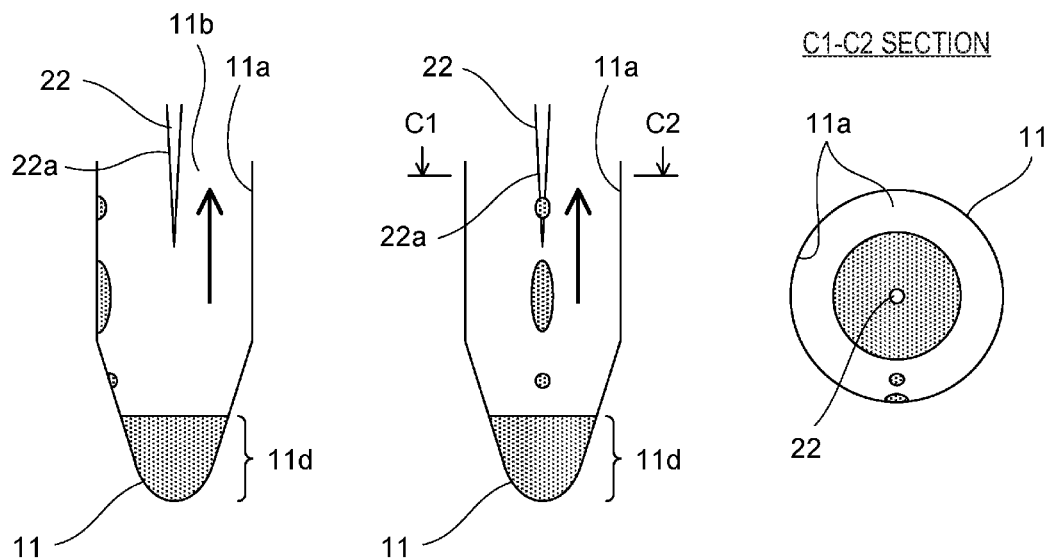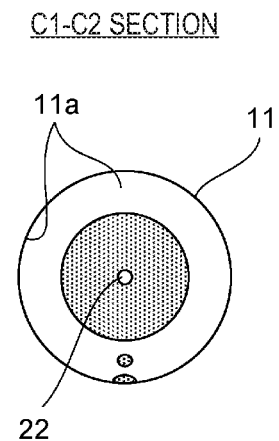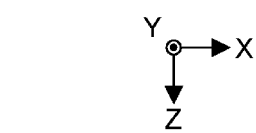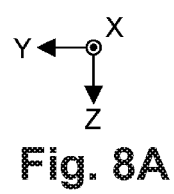
Fig. 8A  Fig. 8B  Fig. 8C
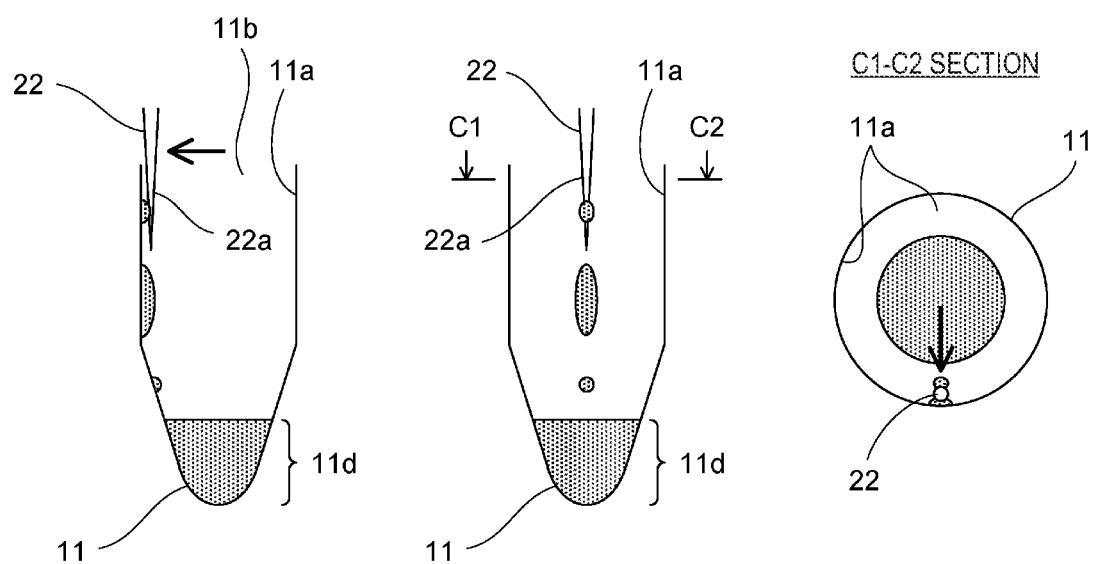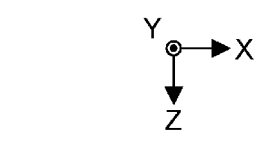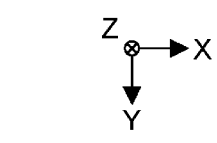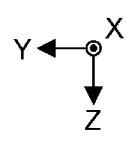
Fig. 8D  Fig. 8E  Fig. 8F

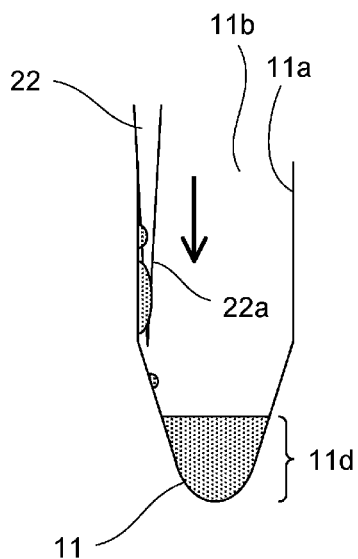
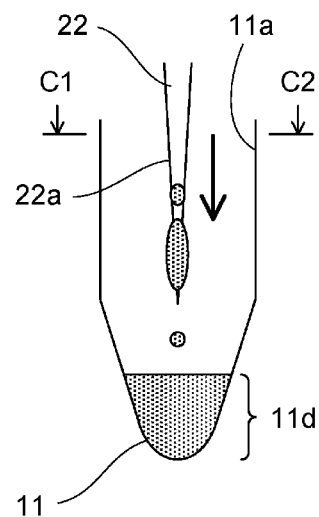
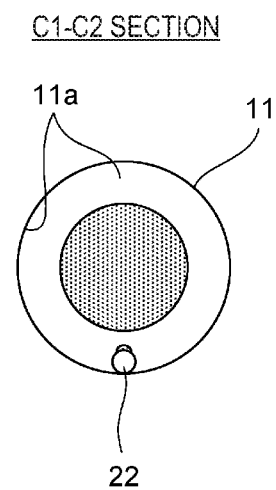
Fig. 9A Fig. 9B Fig. 9C
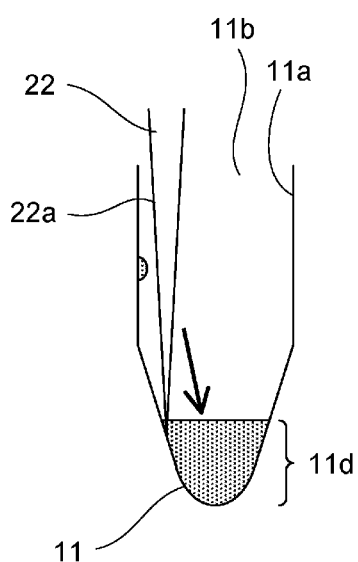
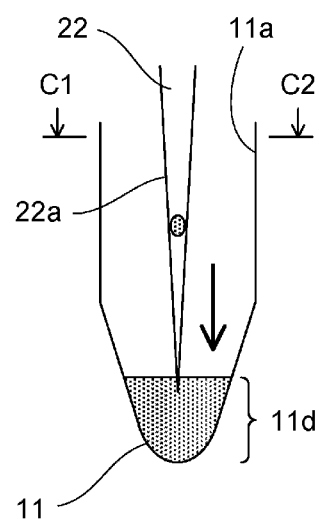
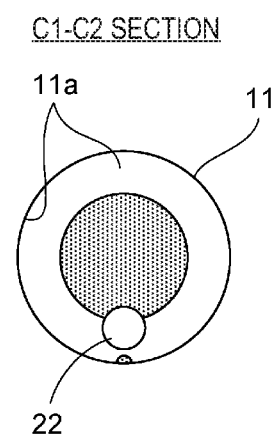
Fig. 9D Fig. 9E Fig. 9F

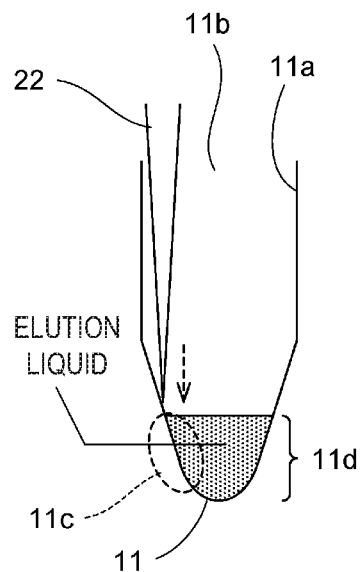
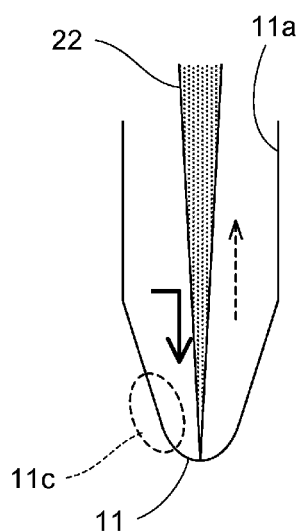
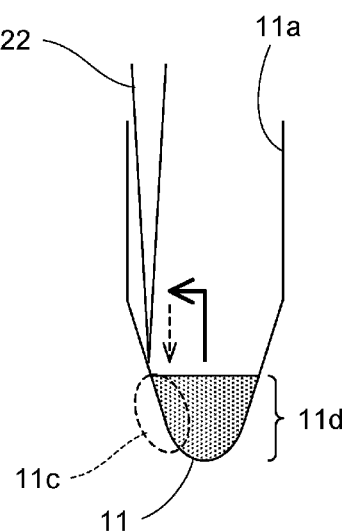
Fig. 24A   Fig. 24B   Fig. 24C
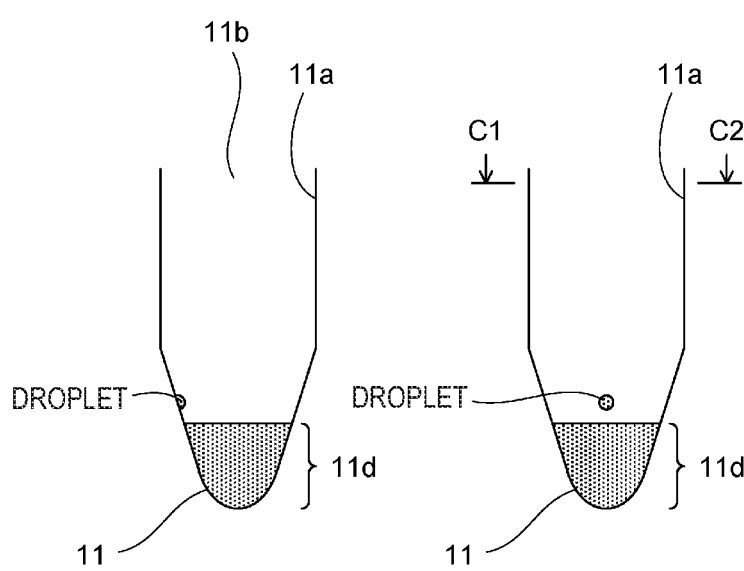
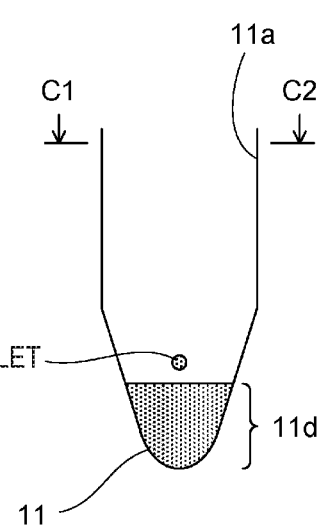
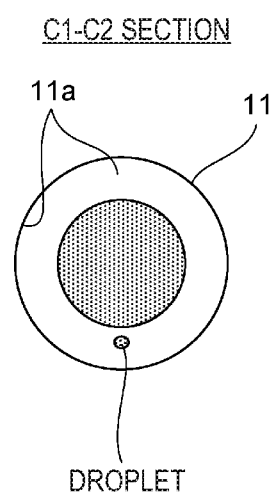
Fig. 24D   Fig. 24E   Fig. 24F

SAMPLE PROCESSING METHOD AND SAMPLE PROCESSING APPARATUS

CROSS REFERENCE TO RELATED APPLICATIONS

This application claims priority from prior Japanese Patent Application No. 2017-015799 filed with the Japan Patent Office on Jan. 31, 2017, the entire contents of which are incorporated herein by reference.

BACKGROUND

The present disclosure relates to a sample processing method and a sample processing apparatus.

Japanese Patent Application Publication No. 2010-533490 (Patent Document 1) describes a method of using magnetic particles to extract nucleic acid as an analyte. In the method of Patent Document 1, as illustrated in FIG. 27, a suspension containing magnetic particles bound with nucleic acid is housed in a container 701. The container 701 is held by a holder 702, and a magnet 703 is moved close to the container 701 to cause the magnetic particles to adhere to the inner wall of the container 701. In this state, the liquid in the container 701 is removed. Thereby, impurities are removed from the container. Then, after the magnet 703 is moved away from the container 701, an elution liquid for releasing the nucleic acid from the magnetic particles is dispensed to the container 701, mixing with the elution liquid is carried out, and the container 701 is heated through the holder 702. As a result, the magnetic particles are detached from the inner wall of the container 701, and the nucleic acid is released from the magnetic particles. The magnet 703 is moved close to the container 701 to cause the magnetic particles to adhere to the inner wall of the container 701, and the liquid in the container 701 is taken out and used for analysis.

In a case where a nucleic acid extracting method includes a step of causing magnetic particles to bind with nucleic acid to adhere to the inner wall of a container like that of Patent Document 1, the magnetic particles bound with the nucleic acid may remain attached to the inner wall of the container and fail to be mixed with the elution liquid. In that case, if the amount of nucleic acid is scarce, a necessary amount of nucleic acid for analysis may not be extracted.

It is preferable to prevent magnetic particles bound with an analyte from remaining on the inner wall of a container.

SUMMARY

A sample processing method according to one or more embodiments may include: removing a liquid component in a container housing a suspension containing a magnetic particle bound with an analyte, while causing magnetic adhesion of the magnetic particle in the container; discharging an elution liquid for releasing the analyte from the magnetic particle from a pipette into the container from which the liquid component has been removed so as to mix the magnetic particle and the elution liquid together; moving, after discharging the elution liquid from the pipette into the container, the pipette relative to and close to an inner wall of the container so as to collect a droplet attached to the inner wall onto an outer surface of the pipette; and moving a tip of the pipette to an accumulation area in which the elution liquid accumulates in the container so as to move the droplet collected on the outer surface of the pipette to the accumulation area.

A sample processing method according to one or more embodiments may include: removing a liquid component in a container housing a first liquid containing a magnetic particle bound with an analyte, while causing magnetic adhesion of the magnetic particle in the container; discharging a second liquid, which is different from the first liquid, from a pipette into the container from which the liquid component has been removed so as to mix the magnetic particle and the second liquid together; moving, after discharging the elution liquid from the pipette into the container, the pipette relative to and close to an inner wall of the container so as to collect a droplet attached to the inner wall onto an outer surface of the pipette; and moving a tip of the pipette to an accumulation area in which the second liquid accumulates in the container so as to the droplet collected on the outer surface of the pipette to the accumulation area.

A sample processing apparatus according to one or more embodiments may include: a dispensing part that includes a pipette and is configured to dispense a liquid via the pipette into a container; a magnetic force application part that includes a magnet and is configured to apply a magnetic force to the container; and a controller. The controller may cause the dispensing part to remove a liquid component in a container housing a suspension containing a magnetic particle bound with an analyte in a condition in which the controller causes the magnetic force application part to apply the magnetic force to the container and cause magnetic adhesion of the magnetic particle in the container. The controller may cause the dispensing part to discharge an elution liquid for releasing the analyte from the magnetic particle via the pipette into the container from which the liquid component has been removed. After the dispensing part discharges the elution liquid into the container, the controller may cause the pipette to move close to an inner wall of the container to collect a droplet attached to the inner wall onto an outer surface of the pipette. The controller may cause the pipette to move to an accumulation area in which the elution liquid accumulates in the container to move the droplet collected on the outer surface of the pipette to the accumulation area.

A sample processing method according to one or more embodiments may include: removing a liquid component in a container housing a suspension containing a magnetic particle bound with an analyte, while causing magnetic adhesion of the magnetic particle in the container; discharging, from a pipette to an attachment area of the inner wall of the container, an elution liquid for releasing the analyte from the magnetic particle; and performing a plurality of times an operation including: aspirating the elution liquid discharged and accumulated in the container; and discharging the aspirated elution liquid to the attachment area of the inner wall of the container on which the magnetic particle is attached. The magnetic particle may be attached on the attachment area of the inner wall of the container from which the liquid component has been removed.

A sample processing apparatus according to one or more embodiments may include: a dispensing part that includes a pipette and is configured to dispense a liquid via the pipette into a container; a magnetic force application part that includes a magnet and is configured to apply a magnetic force to the container; and a controller. The controller may cause the dispensing part to remove a liquid component in a container housing a suspension containing a magnetic particle bound with an analyte in a condition in which the controller causes the magnetic force application part to apply the magnetic force to the container and cause magnetic adhesion of the magnetic particle in the container. The controller may cause the dispensing part to discharge an elution liquid for releasing the analyte from the magnetic particle via the pipette to an attachment area of the inner wall of the container. The magnetic particle may be attached on the attachment area of the inner wall of the container from which the liquid component has been removed. The controller may cause the dispensing part to perform a plurality of times an operation of: aspirating the elution liquid discharged and accumulated in the container; and discharging the aspirated elution liquid to the attachment area of the inner wall of the container.

BRIEF DESCRIPTION OF DRAWINGS

FIGS. 3A and 3B are schematic side views illustrating the configurations of pipettes according to Embodiment 1, and FIG. 3C is a schematic side view illustrating the configuration of a pipette according to a modification of Embodiment 1;

FIGS. 5A to 5C are side and sectional views of a container illustrating droplets at the end of a mixing step according to Embodiment 1, and FIGS. 5D to 5F are side and sectional views illustrating a container in a given state in a droplet collecting step according to Embodiment 1;

FIGS. 7A to 7C are side and sectional views illustrating a container in a given state in a droplet collecting step according to Embodiment 1, and FIGS. 7D to 7F are side and sectional views illustrating a container in a given state in a moving step according to Embodiment 1;

FIGS. 8A to 8C are side and sectional views illustrating a container in a given state in a moving step according to Embodiment 1, and FIGS. 8D to 8F are side and sectional views illustrating a container in a given state in a moving step according to Embodiment 1;

FIGS. 9A to 9C are side and sectional views illustrating a container in a given step in a moving step according to Embodiment 1, and FIGS. 9D to 9F are side and sectional views illustrating a container in a given state in a moving step according to Embodiment 1;

FIGS. 24A to 24C are side views illustrating a container in a given state in a mixing step according to Embodiment 2, and FIGS. 24D to 24F are side and sectional views of a container illustrating droplets at the end of a mixing step according to Embodiment 2;

DETAILED DESCRIPTION

Figure 1:
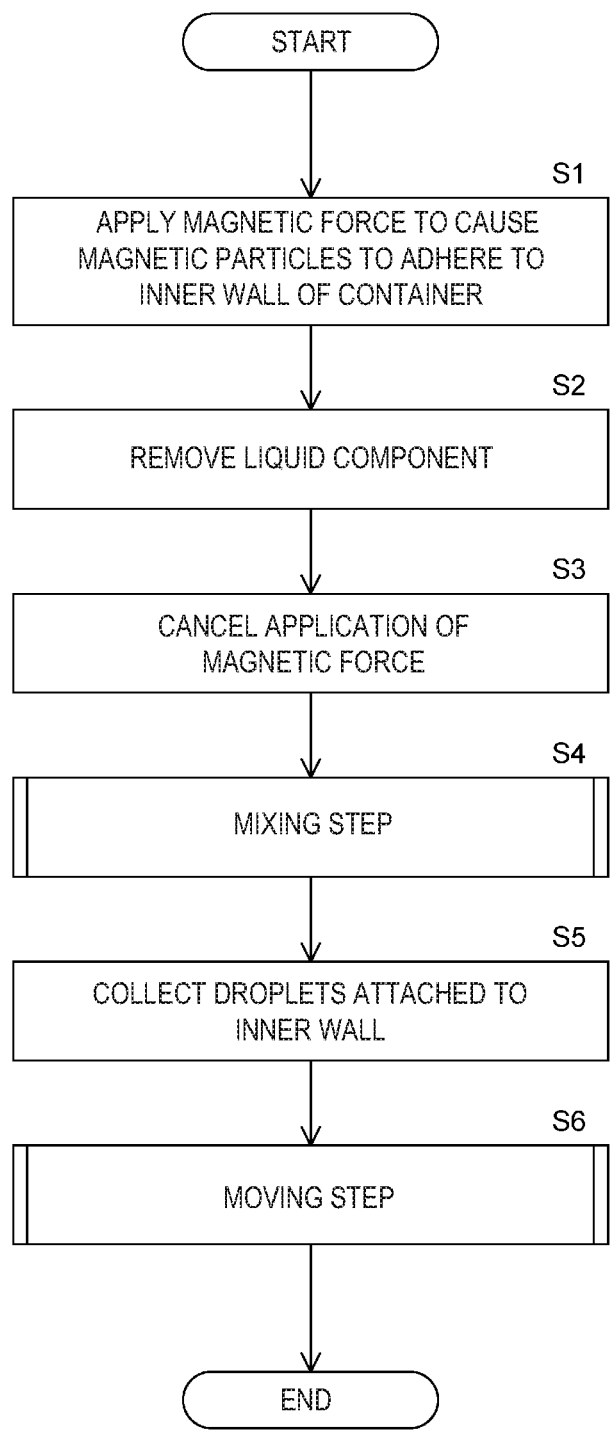
FIG. 1 is a flowchart illustrating a sample processing method according to Embodiment 1.

A sample processing method according to a first aspect may include: removing a liquid component in a container 11 housing a suspension containing a magnetic particle 77 bound with an analyte 71, while causing magnetic adhesion of the magnetic particle 77 in the container 11 (S2); discharging an elution liquid for releasing the analyte 71 from the magnetic particle 77 from a pipette 102 into the container 11 from which the liquid component has been removed so as to mix the magnetic particle 77 and the elution liquid together (S4); moving, after discharging the elution liquid from the pipette 102 into the container 11, the pipette 102 relative to and close to an inner wall 11a of the container 11 so as to collect a droplet attached to the inner wall 11a onto an outer surface 22a of the pipette 102 (S5); and moving a tip of the pipette 102 to an accumulation area 11d in which the elution liquid accumulates in the container 11 so as to move the droplet collected on the outer surface 22a of the pipette 102 to the accumulation area 11d (S6).

According to a sample processing method according to a first aspect, droplets of the elution liquid scattered onto the inner wall 11a of the container 11 may be collected efficiently and moved to the accumulation area 11d. Thereby, droplets containing magnetic particles 77 may be avoided to remain on the inner wall 11a of the container 11, which may increase the number of magnetic particles 77 contained in the accumulation area 11d to enable extraction of a necessary quantity of analytes 71. Further, even when a small amount of elution liquid is dispensed to the container 11 in order to increase the concentration of the analyte 71 in the liquid taken out from the container 11 in the end, a necessary quantity of analytes 71 can be extracted from the container 11 because droplets containing magnetic particles 77 are avoided to remain on the inner wall 11a of the container 11.

Note that the pipette 102 is formed by for example a nozzle which is an apparatus or the like and a pipette tip which is a replaceable part attached to the nozzle. Alternatively, the pipette 102 may be configured as a part of the apparatus or the like.

In a sample processing method according to a first aspect, moving the tip of the pipette 102 to the accumulation area 11d in the container 11 (S6) may include: moving the pipette 102 away from the inner wall 11a (S21); elevating the pipette 102 (S22); moving the pipette 102 close to the inner wall 11a (S23); and lowering the pipette 102 to push down the droplet (S24).

The operations (S21 to S24) in the moving the tip of the pipette 102 to the accumulation area 11d in the container 11 (S6) may be repeatedly executed. Then, even if collected droplets are away from the accumulation area, the droplets can be moved to the accumulation area smoothly and efficiently.

In a sample processing method according to a first aspect, moving the tip of the pipette 102 to the accumulation area 11d (S6) may include moving the tip of the pipette 102 at least to a liquid level of the elution liquid accumulated in the accumulation area 11d.

In a sample processing method according to a first aspect, moving the pipette 102 relative to and close to the inner wall 11a of the container 11 (S5) may include bringing the pipette 102 into contact with the inner wall 11a of the container 11. Then, the pipette 102 can smoothly collect droplets remaining on the inner wall 11a of the container 11.

In a sample processing method according to a first aspect, the pipette 102 may include a nozzle 202 and a pipette tip 22 attached to the nozzle 202. Then, replacement of the pipette tip 22 can omit an operation such as pipette cleaning.

In a sample processing method according to a first aspect, moving the pipette 102 relative to and close to the inner wall 11a of the container 11 (S5) may include moving the nozzle 202, to which the pipette tip 22 is attached, in a direction orthogonal to a center axis of the container 11 with the pipette tip 22 touching the inner wall 11a of the container 11. Then, the pipette tip 22 elastically deforms by being pushed against the inner wall 11a and can be moved along the inner wall 11a. This enables to collect droplets attached to the inner wall 11a efficiently. Further, since the nozzle only needs to be moved linearly, control of the pipette tip can be simplified.

In a sample processing method according to a first aspect, moving the pipette 102 relative to and close to the inner wall 11a of the container 11 (S5) may include moving the nozzle 202, to which the pipette tip 22 is attached, circumferentially along the inner wall 11a of the container 11. With this, collection of droplets attached to the inner wall 11a can be conducted efficiently. This also may prevent the pipette tip 22 from elastically deforming when the pipette tip 22 is moved and thus can maintain the stable attachment state of the pipette tip 22 with respect to the nozzle 202.

In a sample processing method according to a first aspect, discharging the elution liquid from the pipette 102 into the container 11 (S4) may include discharging the elution liquid from the pipette 102 into the container 11 after cancelling application of a magnetic force causing the magnetic adhesion of the magnetic particle 77 in the container 11. Then, magnetic particles 77 attached to the inner wall 11a of the container 11 can be detached easily.

In a sample processing method according to a first aspect, discharging the elution liquid from the pipette 102 into the container 11 (S4) may include discharging the elution liquid from the pipette 102 to an attachment area 11c of the inner wall 11a of the container 11 on which the magnetic particle 77 is attached. Then, magnetic particles 77 attached to the inner wall 11a of the container 11 can be detached from the inner wall 11a.

In a sample processing method according to a first aspect, discharging the elution liquid from the pipette 102 into the container 11 (S4) may include: aspirating the elution liquid accumulated in the accumulation area 11d into the pipette 102; and discharging the aspirated elution liquid to the attachment area 11c (S12). Then, magnetic particles 77 attached to the inner wall 11a of the container 11 can be detached from the inner wall 11a, and also distribution of magnetic particles 77 in the elution liquid can be promoted by the agitation effect produced by the discharge of the elution liquid.

In a sample processing method according to a first aspect, aspirating the elution liquid accumulated in the accumulation area 11d into the pipette 102; and discharging the aspirated elution liquid to the attachment area 11c may be performed a plurality of times. Detachment of magnetic particles from the inner wall 11a of the container 11 and mixing of the magnetic particles 77 and the elution liquid can be performed surely.

In a sample processing method according to a first aspect, discharging the elution liquid from the pipette 102 into the container 11 (S4) may include discharging, after discharging the aspirated elution liquid to the attachment area 11c, another elution liquid that contains no magnetic particle 77 to the attachment area 11c. (S14). This may make it unlikely that a droplet of the elution liquid containing magnetic particles 77 remains on the inner wall 11a of the container 11 and can increase the number of magnetic particles 77 in the accumulation area 11d.

In a sample processing method according to a first aspect, discharging the elution liquid from the pipette 102 into the container 11 (S4) may include discharging the elution liquid from the pipette 102 into the container 11 along the inner wall 11a of the container 11 (S11, S12). This may enable the elution liquid to be properly poured on the magnetic particles 77 attached to the inner wall 11a of the container 11.

A sample processing method according to a first aspect may further include supplying, before removing the liquid component from the container 11 (S2, S404), the suspension into the container 11 (S401). A liquid amount of the elution liquid discharged into the container 11 may be less than a liquid amount of the suspension supplied into the container 11. In this case, since the liquid amount of the elution liquid is small, some of the magnetic particles 77 attached to the inner wall 11*a* of the container 11 are not immersed in the elution liquid when the elution liquid is merely poured into the container 11. Thus, a step is needed for discharging the elution liquid to magnetic particles 77 attached to the inner wall 11*a* of the container 11 to detach the magnetic particles 77 from the inner wall 11*a*. On the other hand, the step of detaching the magnetic particles 77 from the inner wall 11*a* causes the elution liquid containing the magnetic particles to attach to the inner wall 11*a* of the container 77 and decreasing the number of magnetic particles 77 contained in the accumulation area 11*d*. Even in such a case, the sample processing method according to the first aspect can increase the number of magnetic particles 77 contained in the accumulation area 11*d* by moving the elution liquid attached to the inner wall 11*a* of the container 11 to the accumulation area 11*d* as described above.

In a sample processing method according to a first aspect, a magnetic force causing the magnetic adhesion of the magnetic particle 77 in the container 11 may be applied from a side of the container 11. This may prevent magnetic particles from staying on the bottom of the container.

In a sample processing method according to a first aspect, the magnetic force may be applied to at least an area of the container 11 which is larger than the accumulation area 11*d*. Then, when the elution liquid is accumulated in the container 11 after the liquid component of the suspension is removed from the container 11, the range of the magnetic particles 77 attached to the inner wall 11*a* of the container 11 spreads out of the accumulation area 11*d* of the elution liquid, so that some of the magnetic particles 77 attached to the inner wall 11*a* of the container 77 are not immersed in the elution liquid. On the other hand, the sample processing method according to the first aspect produces an effect in such a case.

In a sample processing method according to a first aspect, after moving the tip of the pipette 102 to the accumulation area 11*d* (S6) in the container 11, liquid containing the analyte 71 from the container 11 may be aspirated, while causing magnetic adhesion of the magnetic particle 77 in the container 11. (S411). With this, collection of the analyte may be performed surely.

In a sample processing method according to a first aspect, the analyte (71) may be nucleic acid. For example, the analyte is DNA or nucleic acid other than DNA. An analyte may be any substance as long as it is contained in a sample collected from a living body, and may be, for example, protein.

In this case, the nucleic acid may be cell-free DNA. A plasma sample separated from the blood of a subject includes DNA fragments released from cells, called cell-free DNA (cfDNA). In a plasma sample separated from the blood of a subject with cancer, cancer cell-derived DNA fragments are mixed in a part of the cell-free DNA. There is only a small amount of cell-free DNA in a sample, so in order to increase the efficiency for an analysis to be performed in the following step, the concentration of cell-free DNA in the elution liquid needs to be increased. The sample processing method according to the first aspect enables to extract the necessary amount of cell-free DNA from the container. This enables, for example, a precise determination as to whether blood contains cancer cell-derived DNA fragments. Such a determination result can be utilized to diagnose whether the subject has cancer.

A sample processing method according to a second aspect includes: removing a liquid component in a container 11 housing a first liquid containing a magnetic particle 77 bound with an analyte 71, while causing magnetic adhesion of the magnetic particle 77 in the container 11 (S2); discharging a second liquid, which is different from the first liquid, from a pipette 102 into the container 11 from which the liquid component has been removed so as to mix the magnetic particle 77 and the second liquid together; moving, after discharging the elution liquid from the pipette 102 into the container 11, the pipette 102 relative to and close to an inner wall 11*a* of the container 11 so as to collect a droplet attached to the inner wall 11*a* onto an outer surface 22*a* of the pipette 102; and moving a tip of the pipette 102 to an accumulation area 11*d* in which the second liquid accumulates in the container 11 so as to move the droplet collected on the outer surface 22*a* of the pipette 102 to the accumulation area 11*d* (S6).

According to a sample processing method according to a second aspect, droplets of the different liquid scattered onto the inner wall 11*a* of the container 11 are collected efficiently and moved to the accumulation area 11*d*. Thereby, droplets containing magnetic particles 77 are avoided to remain on the inner wall of the container, which increases the number of magnetic particles 77 contained in the accumulation area 11*d* to enable extraction of a necessary quantity of analytes 71. Further, even when a small amount of elution liquid is dispensed to the container in order to increase the concentration of the analyte 71 in the liquid taken out from the container 11 in the end, a necessary quantity of analytes 71 can be extracted from the container 11 because droplets containing magnetic particles 77 are prevented from remaining on the inner wall 11*a* of the container 11.

A sample processing apparatus 100 according to a third aspect may include: a dispensing part 200 that includes a pipette 102 and is configured to dispense a liquid via the pipette 102 into a container 11; a magnetic force application part 420 that includes a magnet and is configured to apply a magnetic force to the container 11; and a controller 601. The controller 601 may causes the dispensing part 200 to remove a liquid component in a container 11 housing a suspension containing a magnetic particle 77 bound with an analyte 71 in a condition in which the controller 601 causes the magnetic force application part 420 to apply the magnetic force to the container 11 and cause magnetic adhesion of the magnetic particle 77 in the container 11. The controller 601 may cause the dispensing part 200 to discharge an elution liquid for releasing the analyte 71 from the magnetic particle 77 via the pipette 102 into the container 11 from which the liquid component has been removed. After the dispensing part 200 discharges the elution liquid into the container 11, the controller 601 may cause the pipette 102 to move close to an inner wall 11*a* of the container 11 to collect a droplet attached to the inner wall 11*a* onto an outer surface 22*a* of the pipette 102. The controller 601 may cause the pipette 102 to move to an accumulation area 11*d* in which the elution liquid accumulates in the container 11 to move the droplet collected on the outer surface 22*a* of the pipette 102 to the accumulation area 11*d*.

The sample processing apparatus 100 according to the third aspect produces the same or similar effects that produced by the first aspect.

A sample processing method according to a fourth aspect may include: removing a liquid component in a container 11 housing a suspension containing a magnetic particle 77 bound with an analyte 71, while causing magnetic adhesion of the magnetic particle 77 in the container 11 (S2); and discharging, from a pipette 102 to an attachment area 11*c* of the inner wall 11*a* of the container 11, an elution liquid for releasing the analyte 71 from the magnetic particle 77. The magnetic particle 77 may be attached on the attachment area 11c of the inner wall 11a of the container 11 from which the liquid component has been removed (S11). Also, the sample processing method according to the fourth aspect may include performing a plurality of times an operation including: aspirating the elution liquid discharged and accumulated in the container 11; and discharging the aspirated elution liquid to the attachment area 11c of the inner wall 11a of the container 11 on which the magnetic particle 77 is attached (S12, S13).

The sample processing method according to the fourth aspect can effectively detach magnetic particles 77 attached to the inner wall 11a of the container 11 from the inner wall 11a and to mix the magnetic particles 77 with the elution liquid. This may increase the number of magnetic particles 77 contained in the elution liquid, enabling extraction of a necessary quantity of analytes 71. Further, even when a small amount of elution liquid is dispensed to the container 11 in order to increase the concentration of the analyte 71 in the liquid taken out from the container 11 in the end, a necessary quantity of analytes 71 can be extracted from the container 11 because magnetic particles 77 are prevented from remaining on the inner wall 11a of the container 77.

A sample processing apparatus 100 according to a fifth aspect may include: a dispensing part 200 that includes a pipette 102 and is configured to dispense a liquid via the pipette 102 into a container 11; a magnetic force application part 420 that includes a magnet and is configured to apply a magnetic force to the container 11; and a controller 601. The controller 601 may cause the dispensing part 200 to remove a liquid component in a container 11 housing a suspension containing a magnetic particle 77 bound with an analyte 71 in a condition in which the controller 601 causes the magnetic force application part 420 to apply the magnetic force to the container 11 and cause magnetic adhesion of the magnetic particle 77 in the container 11. The controller 601 may cause the dispensing part 200 to discharge an elution liquid for releasing the analyte 71 from the magnetic particle 77 via the pipette 102 to an attachment area 11c of the inner wall 11a of the container 11. The magnetic particle 77 is attached on the attachment area 11c of the inner wall 11a of the container 11 from which the liquid component has been removed. The controller 601 may cause the dispensing part 200 to perform a plurality of times an operation of aspirating the elution liquid discharged and accumulated in the container 11 and discharging the aspirated elution liquid to the attachment area 11c of the inner wall 11a of the container 11.

The sample processing apparatus according to the fifth aspect produces the same or similar effects that produced by the fourth aspect.

According to one or more aspects, droplets containing magnetic particles may be prevented from remaining on the inner wall of the container.

Embodiment 1

In Embodiment 1, one or more aspects are applied to a sample processing method for extracting an analyte from a sample. In Embodiment 1, the analyte is nucleic acid, or more specifically, DNA. The analyte may be any substance contained in a sample collected from a living body. For example, the analyte may be nucleic acid contained in a sample other than DNA and may be protein contained in a sample.

As illustrated in FIG. 1, the sample processing method of Embodiment 1 is a sample processing method for causing DNA, an analyte, to be bound with magnetic particles, collecting the DNA, and then processing the DNA. The method includes processing steps S1 to S6. Step S4, which is a mixing step, includes Steps S11 to S13 illustrated in FIG. 2A. Step S6, which is a moving step, includes Steps S21 to S25 illustrated in FIG. 2B. The steps in FIGS. 1 to 2B may be performed manually by an operator or automatically by a sample processing apparatus. Descriptions for an apparatus configuration and processing steps for a case in which the sample processing apparatus performs the steps in FIGS. 1 to 2B will be given later with reference to FIGS. 11 to 23C.

Hereinbelow, pipettes are used to aspirate and discharge liquid. Embodiment 1 uses a pipette 101 including a pipette tip 21 and a nozzle 201, as illustrated in FIG. 3A, and a pipette 102 including a pipette tip 22 and a nozzle 202, as illustrated in FIG. 3B. The pipette tip 21 and the pipette tip 22 are replaceable parts and attached to the nozzle 201 and the nozzle 202, respectively. The pipette tip 22 is smaller and capable of housing less liquid than the pipette tip 21. The pipette tip 21 and the pipette tip 22 are replaced for liquid aspiration and discharge when necessary.

As illustrated in FIGS. 3A and 3B, the pipette tip 21 and the pipette tip 22 respectively include conical outer surface 21a and conical outer surface 22a, and each of whose diameter gets smaller as it goes down. The outer surface 21a of the pipette tip 21 is a part of the outer surface of the pipette 101, and the outer surface 22a of the pipette tip 22 is a part of the outer surface of the pipette 102. The pipette tip 21 and the pipette tip 22 move when the nozzle 201 and the nozzle 202 move, respectively.

As illustrated in FIG. 3C, a pipette 103 may be used in place of the pipette 101 or the pipette 102. The pipette 103 is a part of the apparatus and is cleaned when necessary for liquid aspiration and discharge. The pipette 103, too, has a conical outer surface 103a whose diameter gets smaller as it goes down.

Figure 2A:
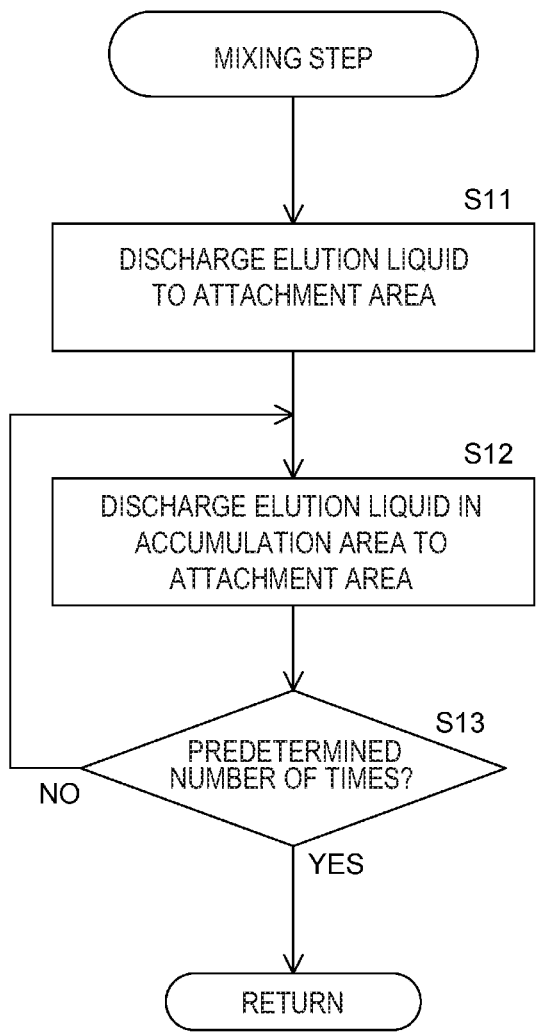
FIG. 2A is a flowchart illustrating a mixing step according to Embodiment 1.
Figure 2B:
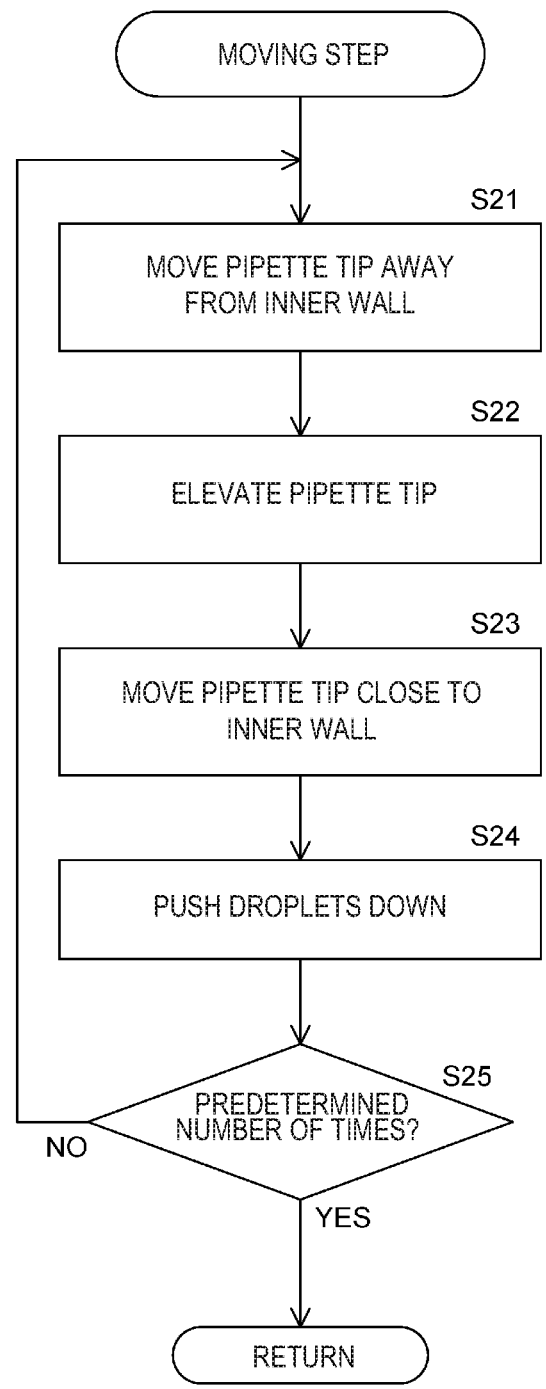
FIG. 2B is a flowchart illustrating a moving step according to Embodiment 1.

In the following, the steps in FIGS. 1 to 2B are described while referring to FIGS. 4A to 10F when necessary. In FIGS. 4A to 10F, the X, Y, and Z axes are orthogonal to one another. The Z-axis positive direction points downward vertically. The X, Y, and Z axes in FIGS. 4A to 10F are the same as those illustrated in FIGS. 3A to 3C.

Figure 4A:
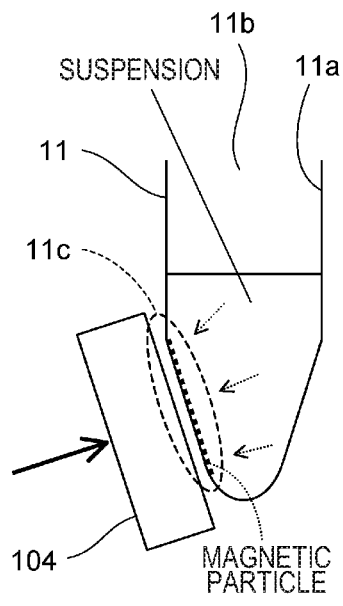
FIGS. 4A to 4C are side views illustrating a container in a given state in a sample processing method according to Embodiment 1.

As illustrated in FIG. 1, in Step S1, in a container housing a suspension containing magnetic particles, the magnetic particles are caused to magnetically adhere to an inner wall 11a of a container 11. More specifically, as illustrated in FIG. 4A, a magnet 104 is moved close to the outer surface of the container 11 from a side, applying magnetic force to the outer surface of the container 11. In other words, the magnet 104 causes magnetic adhesion of the magnetic particles in the container 11. An upper portion of the container 11 is columnar. A lower portion of the container 11 has a slanted surface and is shaped like a cone whose diameter gets smaller as it goes down. The upper end of the container 11 is formed with an opening 11b that makes the inside of the container 11 open upward. In Step S1, the magnetic particles in the suspension adhere to an attachment area 11c. The attachment area 11c is a part of the inner wall 11a of the container 11 which faces the magnet 104.

Note that, in Embodiment 1, the liquid level of the suspension at this time is situated above the upper edge of the attachment area 11c, as illustrated in FIG. 4A. Further, the magnetic force of the magnet 104 is applied to at least an area of the container 11 which is larger than an accumulation area 11d, in which an elution liquid accumulates, to be described later with reference to FIG. 4B.

Figure 4B:
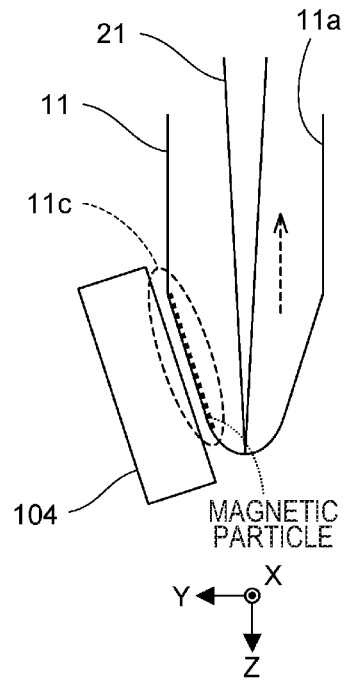
Figure 4C:
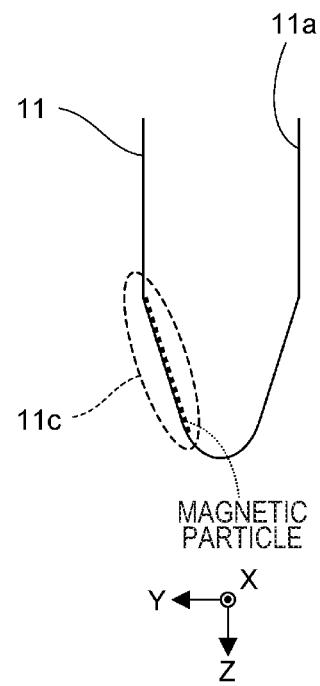

In Step S2, a liquid component is removed from the container 11. More specifically, as illustrated in FIG. 4B, with the magnetic particles in the container 11 magnetically adhering to the attachment area 11c, the pipette tip 21 is inserted into the container 11 through the opening 11b in the Z-axis positive direction, and the liquid in the container 11 is aspirated from a tip, an end or a distal end of the pipette tip 21. Since the magnetic particles attached to the attachment area 11c are being attracted to the attachment area 11c by the magnetic force of the magnet 104, only the liquid component is removed from the container 11. Then in Step S3, the application of the magnetic force to the container 11 is cancelled. More specifically, as illustrated in FIG. 4C, the magnet 104 is moved away from the container 11.

Next, in Step S4, namely a mixing step, elution liquid for releasing DNA from the magnetic particles is discharged from the pipette tip 22 into the container 11 to mix the magnetic particles with the elution liquid.

Figure 4D:
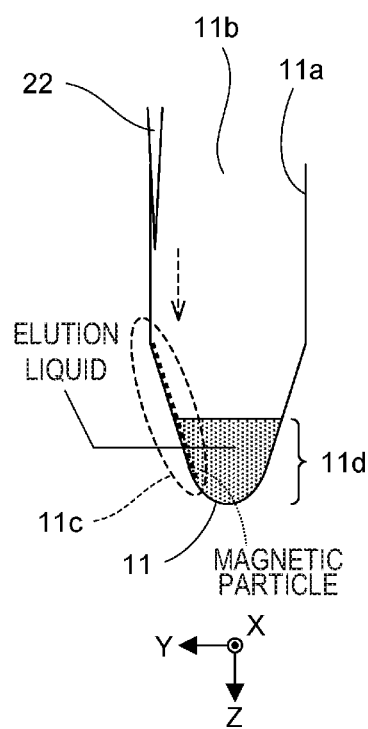
FIGS. 4D to 4F are side views illustrating a container in a given state in a mixing step according to Embodiment 1.

As illustrated in FIG. 2A, in the mixing step, processing of Steps S11 to S13 is performed. In Step S11, elution liquid is discharged from the pipette tip 22 to the attachment area 11c, to which the magnetic particles attach, of the inner wall 11a of the container 11, causing the magnetic particles to be distributed in the elution liquid. More specifically, as illustrated in FIG. 4D, the tip of the pipette tip 22 housing elution liquid is placed above the attachment area 11c, and the elution liquid is discharged from the tip of the pipette tip 22. In other words, the elution liquid is discharged via the pipette tip 22 toward the attachment area 11c in or from the vicinity of an end portion of the container 11 on the opening 11b side. The end portion of the container 11 on the opening 11b side is near, close, or adjacent to the opening 11b. The discharged elution liquid causes the magnetic particles attached to the attachment area 11c to be detached from the attachment area 11c, and a liquid mixture of the elution liquid and the magnetic particles is housed in the lower part of the container 11.

In this way, the discharge of the elution liquid to the magnetic particles attached to the inner wall 11a allows the magnetic particles attached to the inner wall 11a to be detached from the inner wall 11a. Moreover, in a case in which the elution liquid is discharged toward the attachment area 11c from the vicinity of the end portion of the container 11 on the opening 11b side, i.e., from the vicinity of the upper end of the container 11, the elution liquid can be poured properly onto the magnetic particles attached to the inner wall 11a of the container 11.

In order for the liquid taken out from the container 11 in the end after all the steps in FIG. 1 to have a high DNA concentration, a small amount of elution liquid is set to be discharged to the container 11 in Step S11. More specifically, the amount of elution liquid discharged to the container 11 in Step S11 is less than that of the suspension housed in the container 11 in Step S1. Further, in Step S1 in which the magnetic particles are caused to adhere to the inner wall 11a, the magnetic force of the magnet 104 is applied to an area of the container 11 which is larger than the accumulation area 11d in which elution liquid accumulates. The accumulation area 11d is, as illustrated in FIG. 4D, an area in the container 11 where the elution liquid accumulates. More specifically, in a direction parallel the slanted surface of the lower portion of the container 11, the length of the accumulation area 11d in which the elution liquid accumulates is shorter than the length of an area to which the magnetic force of the magnet 104 is applied. In other words, an area of the magnet 104 facing the accumulation area 11d is larger than an area of the accumulation area 11d facing the magnet 104.

Thus, in the example illustrated in FIG. 4D, the liquid level after the discharge of the elution liquid is lower than the upper edge of the attachment area 11c. In a case in which the liquid level is lower than the upper edge of the attachment area 11c, not all the magnetic particles attached to the attachment area 11c are immersed, which makes it likely that some of the magnetic particles remain on the inner wall 11a. However, in Step S11 of Embodiment 1, elution liquid is discharged to the magnetic particles attached to the inner wall 11a, so that the elution liquid detaches the magnetic particles attached to the attachment area 11c. Thus, the magnetic particles are not likely to remain on the inner wall 11a.

Note that Step S4 of the mixing step and its following steps, the pipette tip 22, which is smaller than the pipette tip 21 used in Steps S1 and S2, is used. The reason for this is to precisely dispense a small amount of elution liquid in Step S11 of the mixing step.

Figure 4E:
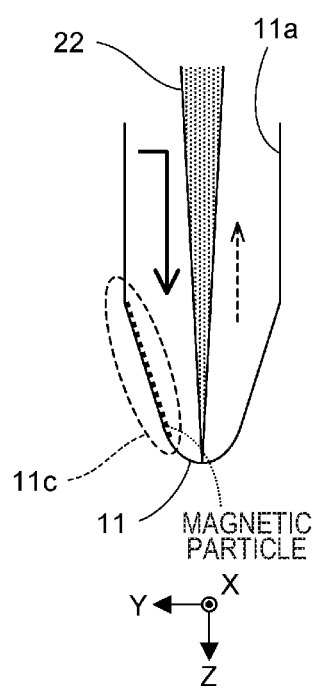
Figure 4F:
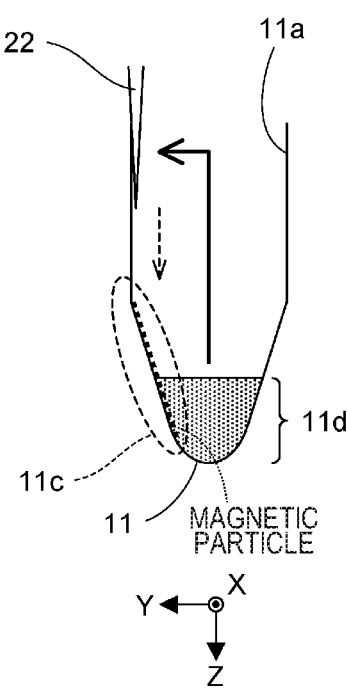

Next, in Step S12, the elution liquid accumulated in the accumulation area 11d is aspirated by the pipette tip 22 and then discharged to the attachment area 11c, to which the magnetic particles attach, of the inner wall 11a. In Step S12, more specifically, as illustrated in FIG. 4E, the tip of the pipette tip 22 is moved to the bottom portion of the container 11 and caused to aspirate the elution liquid in the accumulation area 11d. Then, as illustrated in FIG. 4F, the tip of the pipette tip 22 is placed above the attachment area 11c as it is in FIG. 4D and is caused to discharge the elution liquid. This enables the magnetic particles attached to the inner wall 11a of the container 11 to be detached from the inner wall 11a, and also, promotes mixing of the magnetic particles and the elution liquid by the agitation effect produced by the discharge of the elution liquid.

Although the elution liquid is discharged toward the attachment area 11c in Steps S11 and S12, the elution liquid does not necessarily have to be discharged toward the attachment area 11c if the liquid level of the accumulation area 11d is situated above the upper edge of the attachment area 11c. In this case, for example, the elution liquid is discharged from the tip of the pipette tip 22 situated on the inner wall 11a of the container 11 on the Y-axis negative side. In this case, the magnetic particles on the attachment area 11c are detached from the inner wall 11a by being immersed in the elution liquid in the accumulation area 11d.

Although the entire elution liquid in the container 11 is aspirated and discharged in Step S12 as illustrated in FIGS. 4E and 4F, only a part of the elution liquid in the container 11 may be aspirated and discharged. In other words, the elution liquid may be aspirated leaving a certain amount of elution liquid in the container 11, and the elution liquid may be discharged leaving a certain amount of elution liquid in the pipette tip 22. This helps to prevent, in the mixing step, air bubbles from entering the pipette tip 22 during the aspiration of the elution liquid, and from entering the container 11 during the discharge of the elution liquid.

In Step S13, it is determined whether the processing of Step S12, i.e., the step of discharging the elution liquid accumulated in the accumulation area 11d to the attachment area 11c, has been performed a predetermined number of times. In Embodiment 1, sixty is the predetermined number of times to perform Step S12. If it is determined in Step S13 that the processing of Step S12 has not been performed a predetermined number of times, the processing proceeds back to Step S12 to perform the processing of Step 12 again. If it is determined in Step S13 that the processing of Step S12 has been performed a predetermined number of times, the mixing step is ended.

Performing the processing of Step S12 a plurality of times ensures better detachment of the magnetic particles from the inner wall 11a of the container 11 and better mixing of the magnetic particles with the elution liquid. For example, after Step S12 is performed only once, the magnetic particles may remain on the attachment area 11c as illustrated in FIGS. 4D to 4F. On the other hand, after the processing of Step S12 is performed a plurality of times, the magnetic particles attached to the attachment area 11c can be surely detached and surely mixed with the elution liquid.

In the mixing step, the processing of Step S12 is performed a plurality of times to ensure detachment of magnetic particles from the inner wall 11a and mixing of the magnetic particles with the elution liquid. Nonetheless, droplets of the elution liquid containing the magnetic particles may still be attached to the inner wall 11a as illustrated in FIGS. 5A to 5C. FIGS. 5A to 5C are diagrams illustrating the droplets attached to the inner wall 11a from three different angles. In Steps S5 and S6 performed after the mixing step, the droplets attached to the inner wall 11a as illustrated in FIGS. 5A to 5C are moved to the accumulation area 11d.

Referring back to FIG. 1, in Step S5, the pipette tip 22 is moved in a direction different from the direction for inserting the pipette tip 22 into the container 11, so that the droplets attached to the inner wall 11a are collected onto the outer surface 22a of the pipette tip 22. The direction for inserting the pipette tip 22 into the container 11 is the Z-axis direction. In Embodiment 1, as the direction different from the Z-axis direction, the pipette tip 22 is moved only in directions parallel to the XY plane.

Now, with reference to FIGS. 5D to 7C, a detailed description is given of how the pipette tip 22 is moved in Step S5. Each set of FIGS. 5D to 5F, FIGS. 6A to 6C, FIGS. 6D to 6F, and FIGS. 7A to 7C depicts a given state of the pipette tip 22 being moved.

As illustrated in FIGS. 5D to 5F, first, the pipette tip 22 is placed on the inner wall 11a. More specifically, regarding the position of the pipette tip 22 in the Z-axis direction, the tip of the pipette tip 22 is positioned near the border between the upper portion and the lower portion of the container 11. The position of the pipette tip 22 on the XY plane is almost the same as the position of the attachment area 11c, and is the position where the pipette tip 22 touches the upper end of the inner wall 11a. When the pipette tip 22 is placed on the inner wall 11a in this way, in the example illustrated in FIGS. 5D to 5F, the first and third droplets from the top are touching the outer surface 22a of the pipette tip 22.

Figures 6A, 6B, 6C:
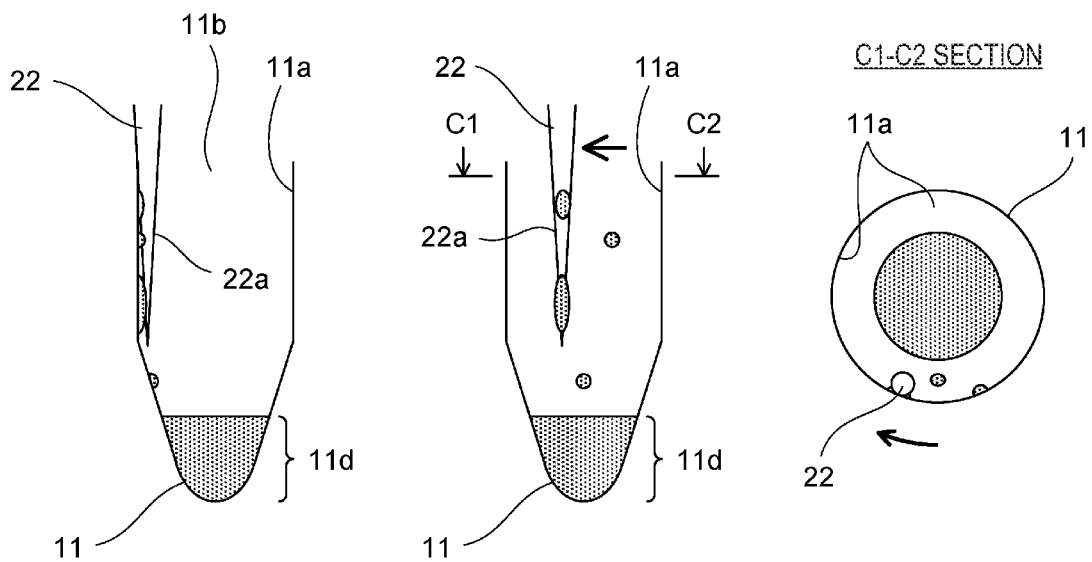
FIGS. 6A to 6C are side and sectional views illustrating a container in a given state in a droplet collecting step according to Embodiment 1.

Next, as illustrated in FIGS. 6A to 6C, the pipette tip 22 touching the inner wall 11a is moved circumferentially along the inner wall 11a. More specifically, as illustrated in FIG. 6C, the pipette tip 22 is moved along the inner wall 11a clockwise when seen in the Z-axis positive direction. In this event, in the example illustrated in FIGS. 6A to 6C, the first and third droplets from the top in FIGS. 5D to 5F move on the inner wall 11a due to surface tension by following the movement of the outer surface 22a of the pipette tip 22. Further, in the example illustrated in FIGS. 6A to 6C, the third and fourth droplets from the top in the FIGS. 5D to 5F are joined into one droplet.

Figures 6D, 6E, 6F:
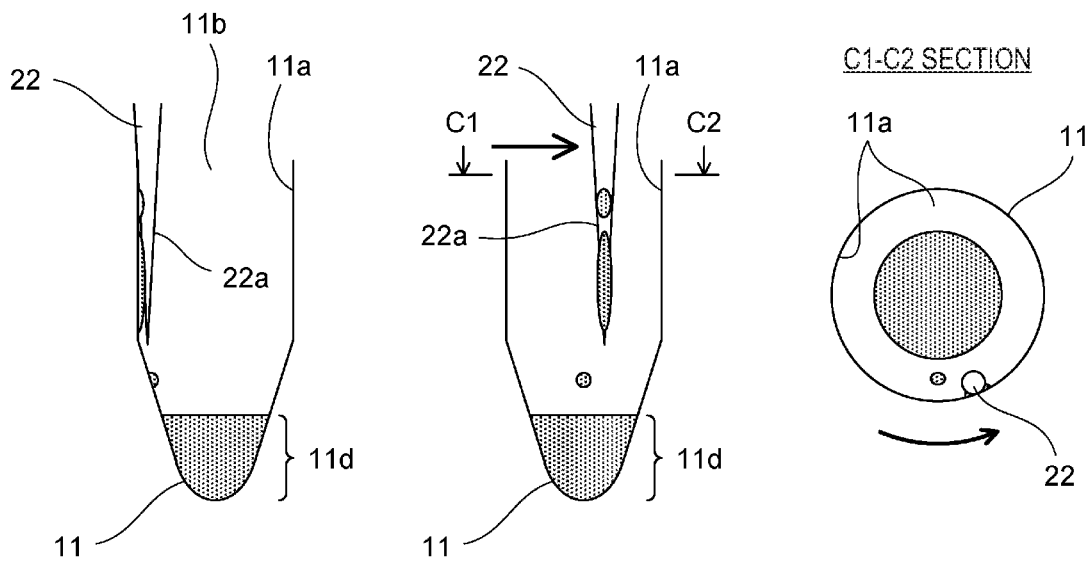
FIGS. 6D to 6F are side and sectional views illustrating a container in a given state in a droplet collecting step according to Embodiment 1.

Next, as illustrated in FIGS. 6D to 6F, the pipette tip 22 touching the inner wall 11a is moved circumferentially along inner wall 11a. More specifically, as illustrated in FIG. 6F, the pipette tip 22 is moved along the inner wall 11a counterclockwise when seen in the Z-axis positive direction. In this event, in the example illustrated in FIGS. 6D to 6F, the first and third droplets from the top in FIGS. 6A to 6C move on the inner wall 11a due to surface tension by following the movement of the outer surface 22a of the pipette tip 22. Further, in the example illustrated in FIGS. 6D to 6F, the second and third droplets from the top in the FIGS. 6A to 6C are joined into one droplet.

Next, as illustrated in FIGS. 7A to 7C, the pipette tip 22 touching the inner wall 11a is moved circumferentially along the inner wall 11a. More specifically, as illustrated in FIG. 7C, the pipette tip 22 is moved along the inner wall 11a clockwise when seen in the Z-axis positive direction. This causes the pipette tip 22 to return to the original position, i.e., the same position as in FIGS. 5D to 5F. In this event, the droplets collected by the circumferential movement of the pipette tip 22 are placed in an end portion of the inner wall 11a on the Y-axis position direction side due to surface tension by following the movement of the outer surface 22a of the pipette tip 22.

In this way, when the pipette tip 22 touching the inner wall 11a is moved in Step S5, the pipette tip 22 enables droplets remaining on the inner wall 11a of the container 11 to be smoothly collected onto the outer surface 22a of the pipette tip 22. Further, by moving in directions parallel to the XY plane, the pipette tip 22 enables droplets scattered on the inner wall 11a to be efficiently collected onto the outer surface 22a of the pipette tip 22. Further, droplets distributed on the XY plane can be collected to a single point, which allows the droplets to move to the accumulation area 11d by merely lowering of the pipette tip 22 in the following Step S6.

Although the pipette tip 22 is moved only in directions parallel to the XY plane in Step S5, the pipette tip 22 may be moved in a direction which is an addition of a direction parallel to the XY plane and the Z-axis direction, i.e., in a slanted direction when the container 11 is seen from the side. In this way, the moving directions of the pipette tip 22 are not limited to directions parallel to the XY plane, and may be any direction as long as they are different from the direction for inserting the pipette tip 22 into the container 11. This complicates the control for the movement of the pipette tip 22, but enables collection of droplets distributed over a larger area.

In addition, although the pipette tip 22 is moved while touching the inner wall 11a in Step S5, the pipette tip 22 may be moved while not touching the inner wall 11a. In this case, the pipette tip 22 is preferably close enough to the inner wall 11a so that droplets attached to the inner wall 11a can touch the outer surface 22a of the pipette tip 22 and move due to surface tension as the pipette tip 22 moves.

Referring back to FIG. 1, in Step S6, namely the moving step, the tip of the pipette tip 22 is moved to the accumulation area 11d to move the droplets collected on the outer surface 22a of the pipette tip 22 to the accumulation area 11d of the elution liquid in the container 11.

As illustrated in FIG. 2B, the moving step includes Step S21 of moving the pipette tip 22 away from the inner wall 11a, Step S22 of elevating the pipette tip 22, Step S23 of moving the pipette tip 22 close to the inner wall 11a, and Step S24 of lowering the pipette tip 22 to push down droplets.

Now, with reference to FIGS. 7D to 10F, a detailed description is given of how the pipette tip 22 is moved in the moving step. Each set of FIGS. 7D to 7F, FIGS. 8A to 8C, FIGS. 8D to 8F, FIGS. 9A to 9C, FIGS. 9D to 9F, FIGS. 10A to 10C, and FIGS. 10D to 10F depicts a given state of the pipette tip 22 being moved.

In Step S21, as illustrated in FIGS. 7D to 7F, the pipette tip 22 is moved away from the inner wall 11a. Next in Step S22, as illustrated in FIGS. 8A to 8C, the pipette tip 22 is elevated. In this event, the tip of the pipette tip 22 is positioned near the end portion of the container 11 on the opening 11b side. Next in Step S23, as illustrated in FIGS. 8D to 8F, the pipette tip 22 is moved close to the inner wall 11a.

Next in Step S24, as illustrated in FIGS. 9A to 9C and FIGS. 9D to 9F, the pipette tip 22 is lowered, pushing down the droplets. In this event, the tip of the pipette tip 22 is lowered to the liquid level of the elution liquid accumulated in the accumulation area 11d. As illustrated in FIGS. 9A to 9C, when the tip of the pipette tip 22 is lowered to near the border between the upper part and the lower part of the container 11, in the example illustrated in FIGS. 9A to 9C, the first drop from the top is pushed down by the pipette tip 22. As illustrated in FIGS. 9D to 9F, when the tip of the pipette tip 22 is lowered to the liquid level of the elution liquid, in the example of FIGS. 9D to 9F, the two droplets from the bottom in FIGS. 9A to 9C are pushed down by the pipette tip 22 and moved to the accumulation area 11d.

In Embodiment 1, as illustrated in FIGS. 9A to 9C, when the tip of the pipette tip 22 is lowered in the Z-axis positive direction to the vicinity of the border between the upper portion and the lower portion of the container 11, the pipette tip 22 touches the end portion of the container 11 on the opening 11b side. The position to which the pipette tip 22 is moved close to the inner wall 11a is determined as illustrated in FIGS. 8D to 8F so that the pipette tip 22 may thus touch the container 11 when being lowered in the Z-axis positive direction. When the pipette tip 22 in FIGS. 9A to 9C is further lowered, in Embodiment 1, the pipette tip 22 is moved in such a direction that the Z-axis positive direction is slightly slanted in the Y-axis negative direction. Thereby, the pipette tip 22 is lowered with the tip of the pipette tip 22 being close to or touching the inner wall 11a.

Note that the nozzle 202 to which the pipette tip 22 is attached may be lowered in the Z-axis positive direction from the state of FIGS. 9A to 9C, so that the pipette tip 22 is lowered while elastically deforming.

Figure 10A:
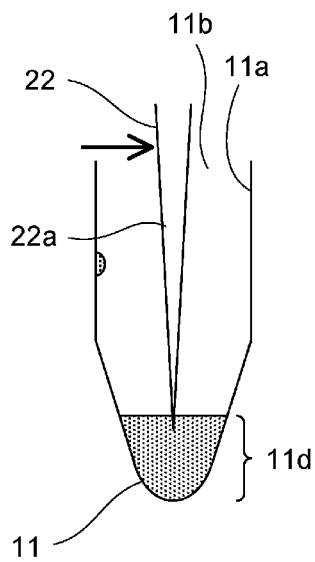
FIGS. 10A to 10C are side and sectional views illustrating a container in a given step in a moving step according to Embodiment 1.
Figure 10B:
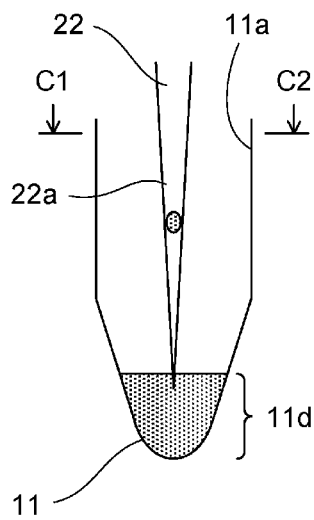
Figure 10C:
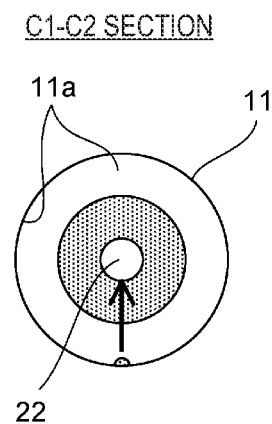
Figure 10D:
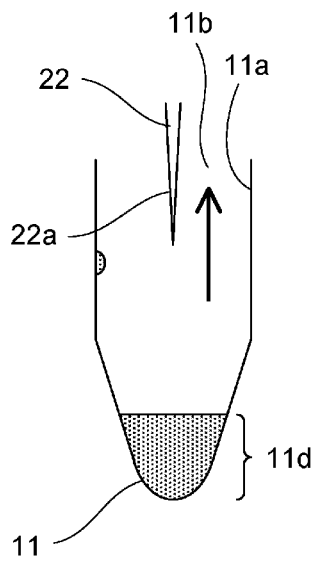
FIGS. 10D to 10F are side and sectional views illustrating the container in a given state in the moving step according to Embodiment 1.
Figure 10E:
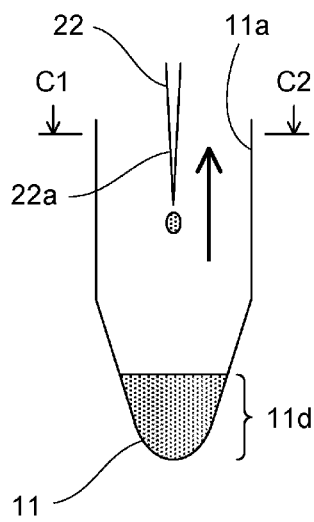
Figure 10F:
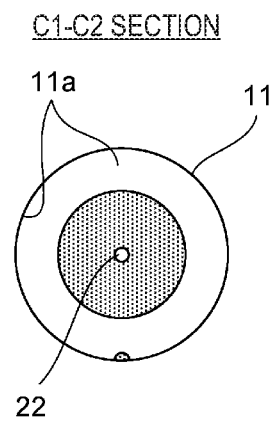

Next, in Step S25, it is determined whether the processing of Steps S21 to S24 has been performed a predetermined number of times. In Embodiment 1, five is the predetermined number for Step S25. If it is determined in Step S25 that the processing of Steps S21 to S24 has not been performed a predetermined number of times, the processing is returned to Step S21 to perform the processing of Steps S21 to S24 again. In Step S21 performed again, the pipette tip 22 is moved away from the inner wall 11a as illustrated in FIGS. 10A to 10C. In the following Step S22, the pipette tip 22 is elevated as illustrated in FIGS. 10D to 10F. Then, the processing of Steps S23 and S24 is performed in the same manner as the above-described procedures.

If it is determined in Step S25 that the processing of Steps S21 to S24 has been performed a predetermined number of times, the pipette tip 22 is moved away from the inner wall 11a and elevated as illustrated in FIGS. 10A to 10F. With this, the moving step is ended.

In the moving step, when the pipette tip 22 is elevated, the droplets do not follow the movement of the pipette tip 22 and move up. Thus, the collected droplets can be efficiently moved to the accumulation area 11d. Further, the processing of Steps S21 to S24 is performed repeatedly, so that even if the droplets collected in Step S5 in FIG. 1 are away from the accumulation area 11d, the droplets can be moved to the accumulation area 11d smoothly and efficiently. Further, in Step S24, the tip of the pipette tip 22 to be moved down is lowered to the liquid level of the elution liquid. When the tip of the pipette tip 22 is thus lowered at least to the liquid level of the elution liquid, the droplets can be brought to the accumulation area 11d more surely.

Note that in Step S24, the tip of the pipette tip 22 to be moved down does not have to be lowered to the liquid level of the elution liquid. Even in this case, once the pipette tip 22 is moved away from the inner wall 11a, the droplets may collect into one round drop and move to the accumulation area 11d by its own weight. However, in order to ensure that the droplets are brought to the accumulation area 11d, it is preferable to lower the tip of the pipette tip 22 to the liquid level of the elution liquid as described above.

In the manner described above, the processing of the steps of the sample processing method illustrated in FIG. 1 ends. When sample processing is performed as described above, droplets of elution liquid scattered onto the inner wall 11a of the container 11 are efficiently collected and moved to the accumulation area 11d. This enables to prevent droplets containing magnetic particles from remaining on the inner wall 11a of the container 11, so that more magnetic particles can be contained in the accumulation area 11d to enable extraction of a necessary amount of DNA. Moreover, since droplets containing magnetic particles are avoided to remain on the inner wall 11a of the container 11, a necessary amount of DNA can be extracted from the container 11 even with a small amount of elution liquid dispensed to the container 11.

Further, as mentioned earlier, in order for the liquid taken out from the container 11 in the end to have a high concentration of DNA, a small amount of elution liquid is set to be discharged to the container 11. In this case, as illustrated in FIG. 4D, not all the magnetic particles attached to the attachment area 11c are immersed in the elution liquid, and some magnetic particles are likely to remain on the inner wall 11a. Even when magnetic particles remain on the inner wall 11a, the mixing step, Step S4, of Embodiment 1 can detach the magnetic particles remaining on the inner wall 11a by repeatedly discharging elution liquid to the attachment area 11c and can mix the magnetic particles with the elution liquid. Moreover, the repeated discharge of elution liquid to the attachment area 11c causes droplets containing magnetic particles to be attached to the inner wall 11a, as illustrated in FIGS. 5A to 5C. Even when such droplets containing magnetic particles are attached to the inner wall 11a, Embodiment 1 collects the droplets in Step S5 and moves the collected droplets to the accumulation area 11d in Step S6, the moving step. This enables to prevent droplets containing magnetic particles from remaining on the inner wall 11a.

Note that in Step S5 of collecting droplets, the pipette tip 22 is moved close to and moved relative to the inner wall 11a of the container 11 secured to the holder of the apparatus or the like, so that droplets attached to the inner wall 11a are collected onto the outer surface 22a of the pipette tip 22. The present invention is, however, not limited to this, and the inner wall 11a of the container 11 may be moved close to and moved relative to the pipette tip 22 with the pipette tip 22 being stationary at a predetermined position, so that droplets attached to the inner wall 11a are collected onto the outer surface 22a of the pipette tip 22. Alternatively, both the inner wall 11a of the container 11 and the pipette tip 22 may be moved close to and moved relative to each other, so that droplets attached to the inner wall 11a are collected onto the outer surface 22a of the pipette tip 22. In other words, there is no limitation in Step S5 as long as the pipette tip 22 gets close to and moves with respect to the inner wall 11a of the container 11 relatively, so that droplets attached to the inner wall 11a can be collected onto the outer surface 22a of the pipette tip 22.

Further, liquid housed in the container 11 at the initial point of Step S1 may be any liquid as long as it contains magnetic particles, which may be a reagent or a cleaning liquid used in the process of processing an analyte. Also, the liquid discharged to the container 11 in Step S4 is not limited to elution liquid for releasing DNA from magnetic particles, which may be a reagent or a cleaning liquid used in the process of processing an analyte.

<Sample Processing Apparatus>

Next, a description is given of a sample processing apparatus 100 that performs the sample processing method illustrated in FIG. 1.

A plasma sample separated from the blood of a subject contains DNA fragments released from cells, called cell-free DNA (cfDNA). In a plasma sample separated from the blood of a subject with cancer, cancer cell-derived DNA fragments are mixed in a part of such cell-free DNA. Cancer cell-derived DNA fragments are called ctDNA (circulating tumor DNA). The sample processing apparatus 100 extracts DNA from a plasma sample, targeting cell-free DNA as an analyte. After the sample processing apparatus 100 extracts DNA, genetic detection is carried out based on a BEAMing (Bead, Emulsion, Amplification, and Magnetics) method. Thus, the sample processing apparatus 100 of Embodiment 1 extracts DNA as the pretreatment before the genetic detection.

Genetic detection based on the DNA extracted by the sample processing apparatus 100 can determine whether the blood contains cancer cell-derived DNA fragments. Such a determination result can be utilized to, for example, diagnose whether a subject has cancer.

There is only a small amount of cell-free DNA in a sample, so in order to increase the efficiency for the analysis to be performed in the following steps based on a PCR method, the concentration of cell-free DNA needs to be high in elution liquid. The sample processing apparatus 100 uses the above-described sample processing method to enable extraction of a necessary amount of cell-free DNA. This enables a precise determination as to whether blood contains cancer cell-derived DNA fragments.

In the following, elements of the sample processing apparatus 100 that have the same configurations as those illustrated in FIGS. 1 to 10F are denoted by the same reference numerals as those used in FIGS. 1 to 10F for convenience reasons.

Figure 11:
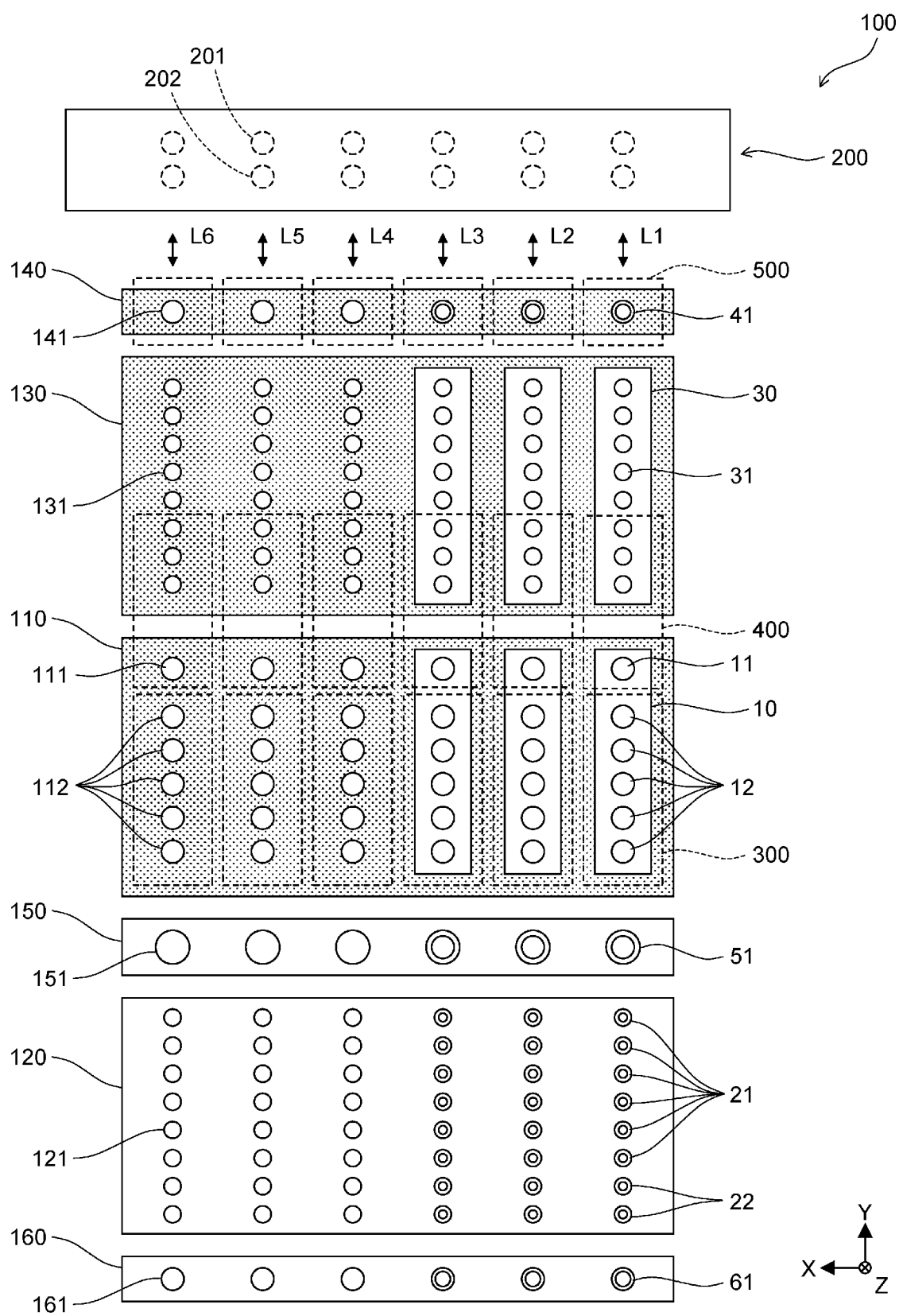
FIG. 11 is a schematic top view illustrating the internal configuration of a sample processing apparatus of Embodiment 1.

As illustrated in FIG. 11, the sample processing apparatus 100 includes plate members 110, 130, and 140, holder members 120, 150, and 160, a dispensing part 200, six reaction parts 300, six elution parts 400, and six cooling parts 500. The XYZ axes in FIG. 11 are the same as those in FIGS. 3A to 10F. In FIG. 11, the X-axis positive direction points to the left, the Y-axis positive direction points to the back, and the Z-axis positive direction points down vertically. The XYZ axes in the following drawings are also the same as those in FIG. 11.

Each plate member 110, 130, and 140 has holes formed therein as will be described below. Each holder member 120, 150, and 160 has hole-shaped holders recessed from the upper surface. These holes and holders are arranged along rows L1 to L6 extending in the Y-axis direction. The rows L1 to L6 are arranged one after another in the X-axis positive direction in the sample processing apparatus 100. Each set of the holes and the holders arranged along any of the rows L1 to L6 corresponds to a processing area for one sample. Thus, the sample processing apparatus 100 has six plasma sample processing areas.

The plate member 110 has one hole 111 and five holes 112 formed along each of the rows L1 to L6. The holes 111 and 112 penetrate the plate member 110. To set one processing cartridge 10, one container 11 and five containers 12 are inserted through, respectively, the one hole 111 and the five holes 112 arranged in the Y-axis direction. Then, the container 11 is supported under the plate member 110 by the corresponding elution part 400 having a hole-shaped holder, and the five containers 12 are supported under the plate member 110 by the corresponding reaction part 300 having holders. The processing cartridge 10 is thus set in the plate member 110. Six of the processing cartridge 10 can be set in the plate member 110 along the rows L1 to L6, respectively.

To start processing a plasma sample, a new processing cartridge 10 is set in advance in the position in line with one of the rows L1 to L6 where a sample container 51 is set. The configuration of the processing cartridge 10 will be described later with reference to FIG. 12A.

The holder member 120 has eight of holder 121 formed along each of the rows L1 to L6. Each holder 121 is hole-shaped, recessed downward from the upper surface of the holder member 120. Six holders 121 arranged on the Y-axis positive side out of the eight holders 121 arranged in the Y-axis direction hold the pipette tips 21. Two holders 121 arranged on the Y-axis negative side out of the eight holders 121 arranged in the Y-axis direction hold the pipette tips 22. The holder member 120 can hold thirty-six pipette tips 21 and twelve pipette tips 22 at positions in the rows L1 to L6. To start plasma sample processing, new pipette tips 21 and 22 are set in advance in the holders 121 in the rows L1 to L6 where the sample container 51 is set.

The plate member 130 has eight of holder 131 formed along each of the rows L1 to L6. Each holder 131 is a hole provided in the plate member 130. Each holder 131 penetrates the plate member 130. To set one reagent cartridge 30, eight of container 31 of the reagent cartridge 30 are inserted through the respective eight of holder 131. Then, the flat portion of the reagent cartridge 30 is supported on the upper surface of the plate member 130. The reagent cartridge 30 is thus set in the plate member 130. Six of reagent cartridge 30 can be set in the plate member 130 along the rows L1 to L6, respectively.

To start plasma sample processing, the reagent cartridge 30 housing reagent is set in advance in the position in line with the rows L1 to L6 where the sample container 51 is set. The configuration of the reagent cartridge 30 will be described later with reference to FIG. 12B.

The eight of the container 31 in the reagent cartridge 30 contain, respectively, solubilizing liquid, preparation liquid, extraction liquid, magnetic-particle suspended reagent, first cleaning liquid, second cleaning liquid, third cleaning liquid, and elution liquid. The preparation liquid, the extraction liquid, and the magnetic-particle suspended reagent are reagents for causing DNA in a plasma sample to be adsorbed, bound or adhered to magnetic particles. The elution liquid is a reagent for releasing the DNA adhered to the magnetic particles.

For example, the solubilizing liquid includes Tris-HCl, EDTA-2Na, Guanidine Thiocyanate, and Tween (registered trademark) 20. The extraction liquid includes Tris-HCl, EDTA-2Na, Guanidine Thiocyanate, and Tween (registered trademark) 20. The preparation liquid includes Isopropanol. The magnetic-particle suspended reagent includes Sodium Azide and magnetic particles, to which DNA in a plasma sample is to be adhered. The magnetic particles are particles with magnetic properties, whose surfaces are covered with silica. The magnetic particles are formed by, for example, iron oxide particles. The first cleaning liquid includes EDTA-2Na, Guanidine Hydrochloride, Sodium Azide, and Ethanol. The second cleaning liquid includes Sodium Azide and Ethanol. The third cleaning liquid includes Ethanol. The elution liquid includes Tris-HCl, EDTA-2Na, and Sodium Azide.

The plate member 140 has holes 141 formed in the respective positions in line with the rows L1 to L6. The holes 141 penetrate the plate member 140. To set a reagent container 41, the reagent container 41 is inserted through one of the holes 141. Then, the reagent container 41 is supported under the plate member 140 by the corresponding cooling part 500 having a hole-shaped holder. The reagent container 41 is thus set in the plate member 140. Six reagent containers 41 can be set in the plate member 140 in the respective positions in line with the rows L1 to L6. To start plasma sample processing, the reagent container 41 housing reagent is set in advance in the position in line with the rows L1 to L6 where the sample container 51 is set. The reagent container 41 houses Proteinase K. The reagent container 41 housing Proteinase K is cooled by the cooling part 500 until the Proteinase K is dispensed.

The holder member 150 has hole-shaped holders 151 at respective positions in line with the rows L1 to L6. The holder 151 holds the sample container 51. The holder member 150 can hold six of the sample container 51 at the respective positions in line with the rows L1 to L6. To start plasma sample processing, the sample container 51 housing a plasma sample is set in advance in a corresponding one of the holders 151.

The holder member 160 has hole-shaped holders 161 formed in the respective positions in line with the rows L1 to L6. The holder 161 holds a container 61. The holder member 160 can hold six of the container 61 at respective positions in line with the rows L1 to L6. To start plasma sample processing, a new container 61 is set in advance in a corresponding one of the holders 161 on one of the rows L1 to L6 where the sample container 51 is set. Into the container 61, DNA-containing liquid extracted in the end is discharged.

The dispensing part 200 includes a pair of the nozzle 201 and the nozzle 202 at each of the positions of the rows L1 to L6. The dispensing part 200 has a configuration to move the nozzle 201 and the nozzle 202 in the Y-axis direction and the Z-axis direction. Each nozzle 201 and nozzle 202 has a columnar-shaped lower end. When the nozzle 201 is placed directly above the pipette tip 21 held by the holder member 120 and is then lowered, the pipette tip 21 is attached to the lower end of the nozzle 201. Similarly, when the nozzle 202 is placed directly above the pipette tip 22 held by the holder member 150 and is then lowered, the pipette tip 22 is attached to the lower end of the nozzle 202. The sample processing apparatus 100 also includes a discarding part (not shown in a figure) for discarding the pipette tip 21 and the pipette tip 22 attached to the nozzle 201 and the nozzle 202. When the nozzle 201, 202 is moved in the Y-axis direction while being in a hole of the discarding part, the pipette tip 21, 22 comes off from the lower end of the nozzle 201, 202 and is collected by the discarding part.

The dispensing part 200 is also configured to be capable of dispensing a plasma sample and reagent via the pipette tip 21 and the pipette tip 22. With the pipette tip 21, 22 attached to the nozzle 201, 202, the dispensing part 200 lowers the tip of the pipette tip 21, 22 to the liquid level and aspirates the liquid. After the aspiration, the dispensing part 200 moves the tip of the pipette tip 21, 22 into a discharge target container, and discharges the liquid aspirated and housed in the pipette tip 21, 22 into the discharge target container. To discard the aspirated liquid, the dispensing part 200 discharges the liquid housed in the pipette tip 21, 22 into a discarding part (not shown in the figure). The configuration of the dispensing part 200 is described later with reference to FIG. 13.

Six of the reaction part 300 are placed under the plate member 110 and are arranged along the rows L1 to L6, respectively. For each reaction part 300, five containers 12 of one processing cartridge 10 are placed. The reaction part 300 heats the containers 12 placed and promotes the reaction between the plasma sample and the reagent in the containers 12. The configuration of the reaction part 300 is described later with reference to FIG. 14.

Six of the elution part 400 are placed under the plate member 110 and the plate member 130, and are arranged along the rows L1 to L6, respectively. For each elution part 400, the container 11 of one processing cartridge 10 is placed. The elution part 400 performs processing to remove impurities adhered to the magnetic particles in the container 11 placed as well as processing to extract DNA by separating the DNA from the magnetic particles. The configuration of the elution part 400 is described later with reference to FIG. 14.

Six of the cooling part 500 are placed under the plate member 140, and are arranged at the respective positions in line with the rows L1 to L6. For each cooling part 500, one reagent container 41 is placed. The cooling part 500 cools the reagent container 41 placed, to a predetermined temperature.

Figure 12A:
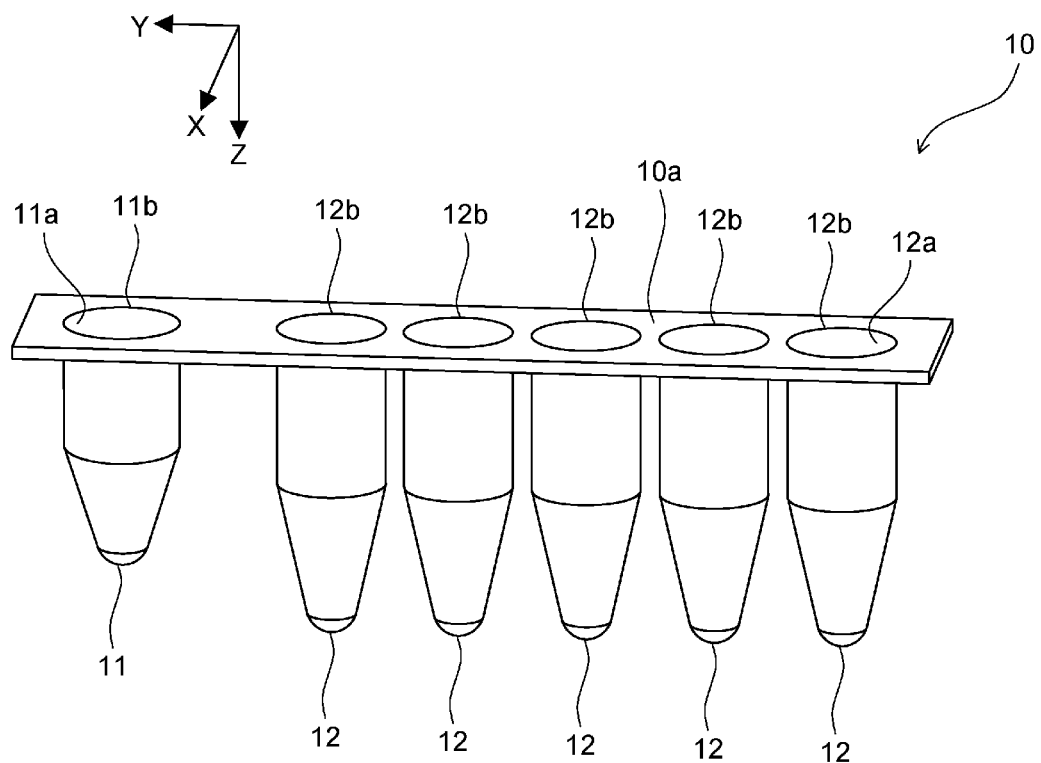
FIG. 12A is a perspective view illustrating the structure of a processing cartridge according to Embodiment 1.

As illustrated in FIG. 12A, the processing cartridge 10 includes a flat portion 10a extending in the Y-axis direction, one container 11, and five containers 12. The containers 11 and 12 are integrally formed via the flat portion 10a. The containers 11 and 12 are formed on the lower surface side of the flat portion 10a. To house liquid inside, the container 11 includes an inner wall 11a, and each container 12 includes an inner wall 12a. Each of the containers 11 and 12 has an opening 11b or an opening 12b formed in its upper portion. Through the opening 11b, the pipette tip 21 or the pipette tip 22 is inserted from above into the container 11 in the Z-axis positive direction. Through the opening 12b, the pipette tip 21 is inserted from above into the container 12 in the Z-axis positive direction.

The inner wall 11a of the container 11 has the same diameter as the opening 11b for its part extending from the opening 11b to a predetermined depth position. The inner wall 11a of the container 11 has a smaller and smaller diameter as it goes in the Z-axis positive direction from this depth position, and connects to the spherically recessed bottom. In other words, the container 11 has a columnar inner surface, a conical inner surface, and a spherically recessed bottom surface. Like the container 11, each container 12 has a columnar inner surface, a conical inner surface, and a spherically recessed bottom surface. The diameter and the depth of the container 12 are different from those of the container 11. The container 12 has a larger capacity than the container 11.

Note that the sample processing apparatus 100 may be equipped with the containers 11 and 12 in advance. In this case, each container is washed for every plasma sample to be used. In this case, however, if a plasma sample remains in the container due to incomplete washing, a plasma sample to be processed next may end up containing a different plasma sample. To avoid such a risk, in Embodiment 1, a new processing cartridge 10 is set when plasma sample processing is to be started.

Figure 12B:
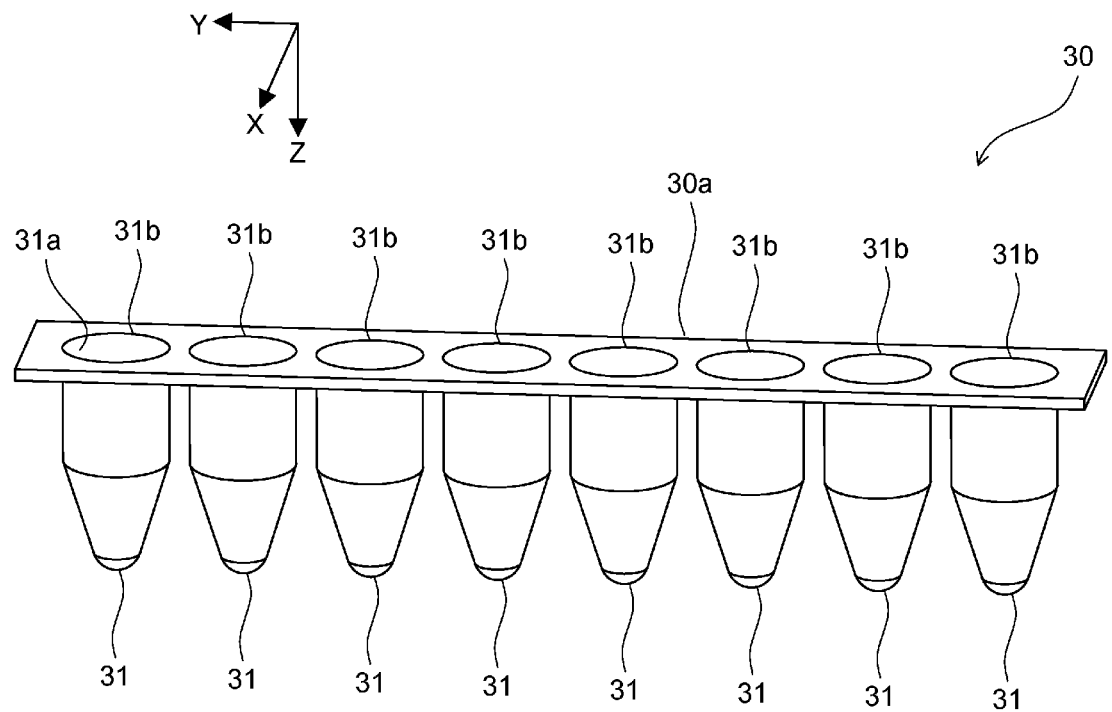
FIG. 12B is a perspective view illustrating the structure of a reagent cartridge according to Embodiment 1.

As illustrated in FIG. 12B, the reagent cartridge 30 includes a flat portion 30a extending in the Y-axis direction and eight containers 31. The containers 31 and the flat portion 30a are integrally formed. The containers 31 are formed on the lower surface side of the flat portion 30a and all have the same shape. Each container 31 includes an inner wall 31a to house liquid therein. Each container 31 has an opening 31b formed in its upper portion. Through the opening 31b, the pipette tip 21 or the pipette tip 22 is inserted into the container 31 from above in the Z-axis positive direction. Like the container 11 in FIG. 12A, each container 31 has a columnar inner surface, a conical inner surface, and a spherically recessed bottom surface.

Figure 13:
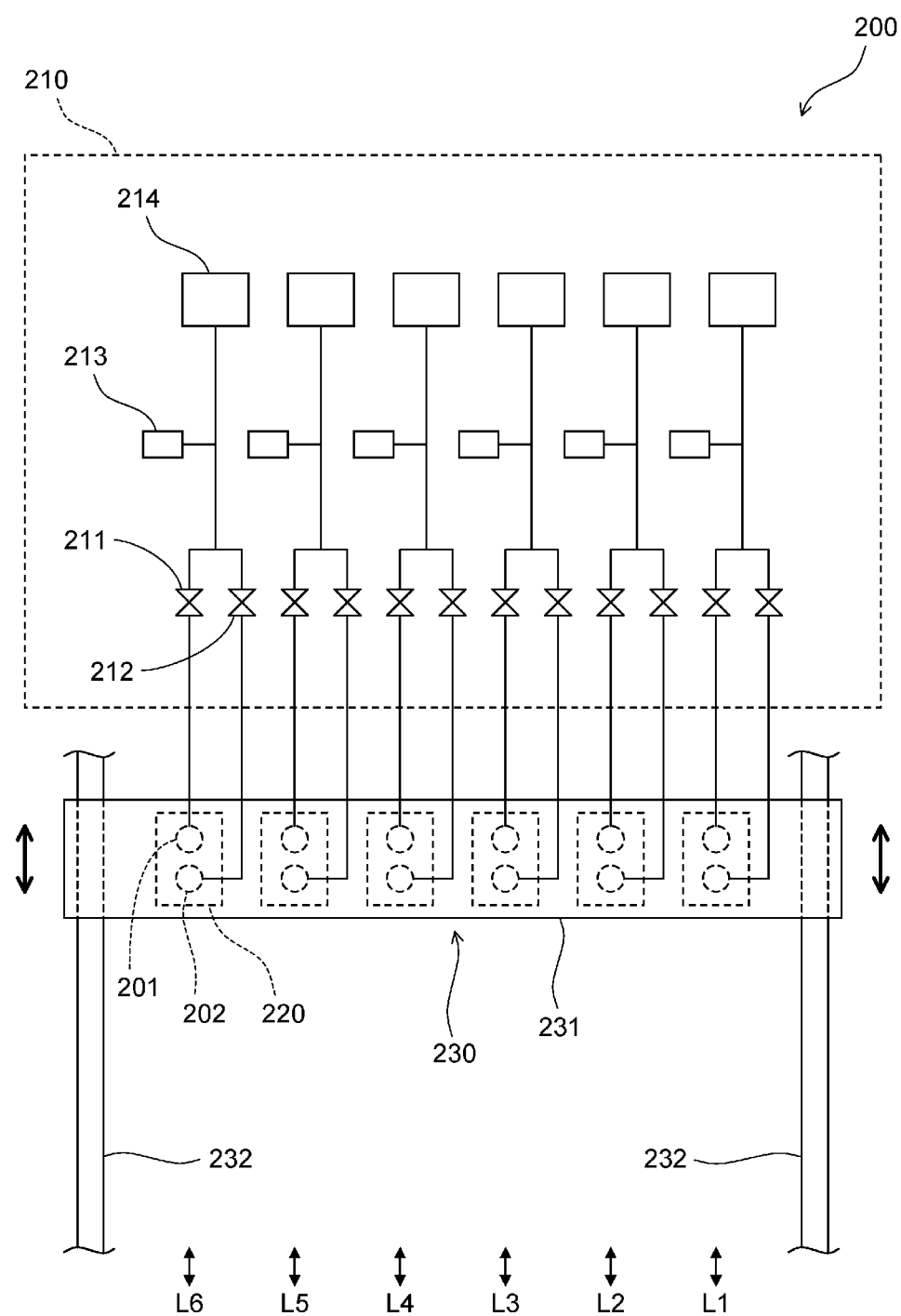
FIG. 13 is a schematic top view illustrating the configuration of a dispensing part according to Embodiment 1.

As illustrated in FIG. 13, the dispensing part 200 includes the nozzle 201, the nozzle 202, a pressure application unit 210, six of an up-and-down transporter 220, and a front-and-back transporter 230.

The pressure application unit 210 includes six valves 211, six valves 212, six pressure sensors 213, and six pumps 214. The valves 211 and the valves 212 are connected to the nozzles 201 and the nozzles 202, respectively, through flow channels. When the pump 214 is driven with the valve 211 opened and the valve 212 closed, liquid can be dispensed through the pipette tip 21 attached to the nozzle 201. When the pump 214 is driven with the valve 211 closed and the valve 212 opened, liquid can be dispensed through the pipette tip 22 attached to the nozzle 202. Each pressure sensor 213 detects the pressure in the flow channels connecting the pump 214 and the valves 211 and 212.

Six of the up-and-down transporter 220 are placed on the lower surface side of a support 231 to coincide in position with the pairs of the nozzles 201 and 202 provided along the rows L1 to L6, respectively. Each up-and-down transporter 220 includes a motor (not shown in the figure), and by driving the motor, transports the corresponding nozzles 201 and 202 up and down. Six of the up-and-down transporter 220 can be driven individually. This enables plasma samples and reagent placed in the rows L1 to L6 to be dispensed individually. The front-and-back transporter 230 includes the support 231 and two rails 232. The front-and-back transporter 230 includes a motor (not shown in the figure) and by driving the motor, transports the support 231 in the Y-axis direction along the rails 232.

Figure 15:
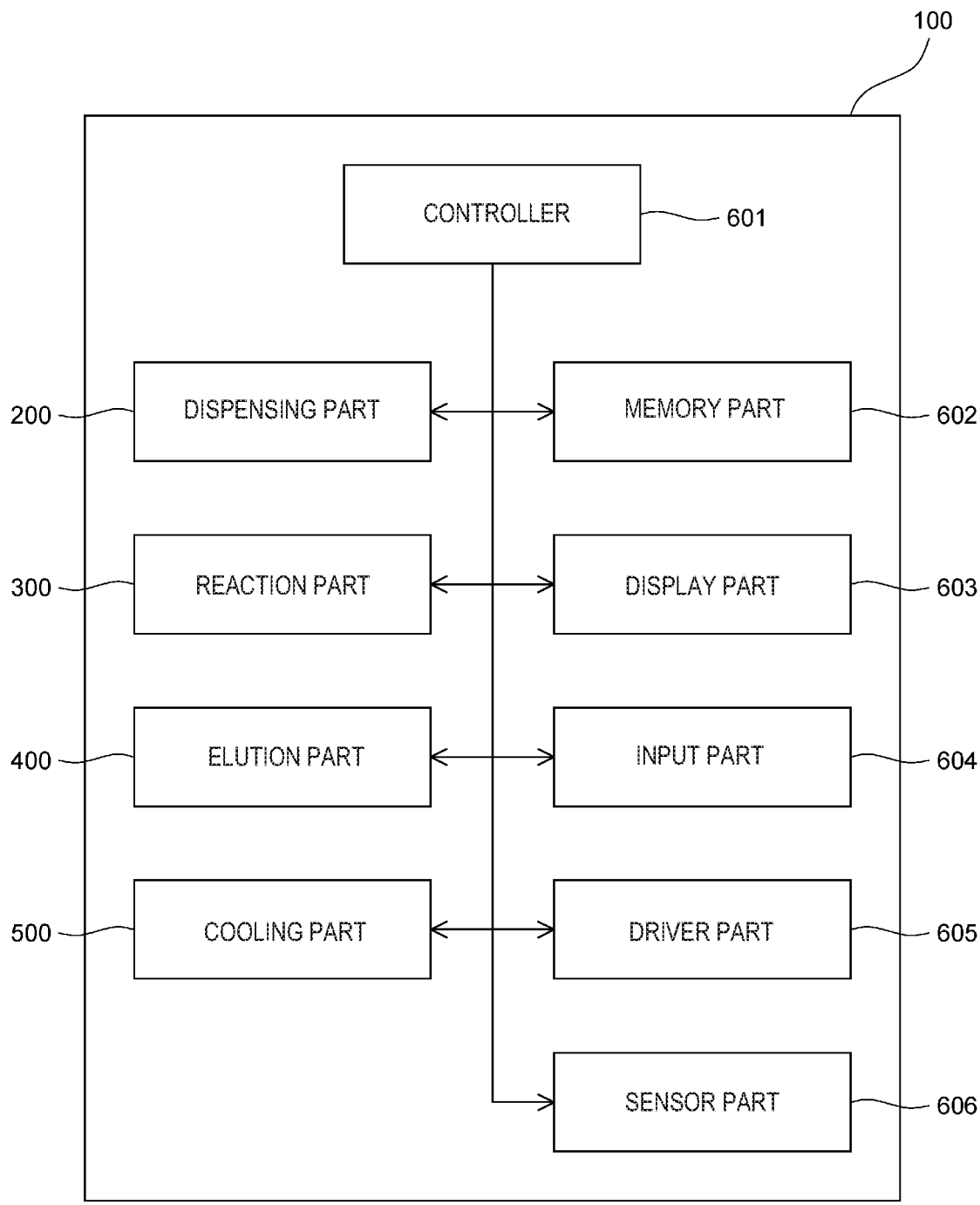
FIG. 15 is a block diagram illustrating the configuration of a sample processing apparatus according to Embodiment 1.

The dispensing part 200 is driven by a controller 601 illustrated in FIG. 15. To aspirate liquid, the controller 601 controls the dispensing part 200 so that the pipette tip 21, 22 is lowered from above the liquid level. When the tip of the pipette tip 21, 22 touches the liquid level, the pressure in the flow channel connecting the pump 214 and the valves 211 and 212 changes. Based on the change in detection signals from the pressure sensor 213, the controller 601 detects that the tip of the pipette tip 21, 22 has touched the liquid level. The controller 601 then controls the dispensing part 200 so that the nozzle 201, 202 is moved down according to the amount to be dispensed and aspirates a predetermined amount of liquid via the pipette tip 21, 22. To discharge liquid, the controller 601 controls the dispensing part 200 so that the tip of the pipette tip 21, 22 is placed inside the discharge target container. The controller 601 then controls the dispensing part 200 so that the liquid housed in the pipette tip 21, 22 is discharged.

Figure 14:
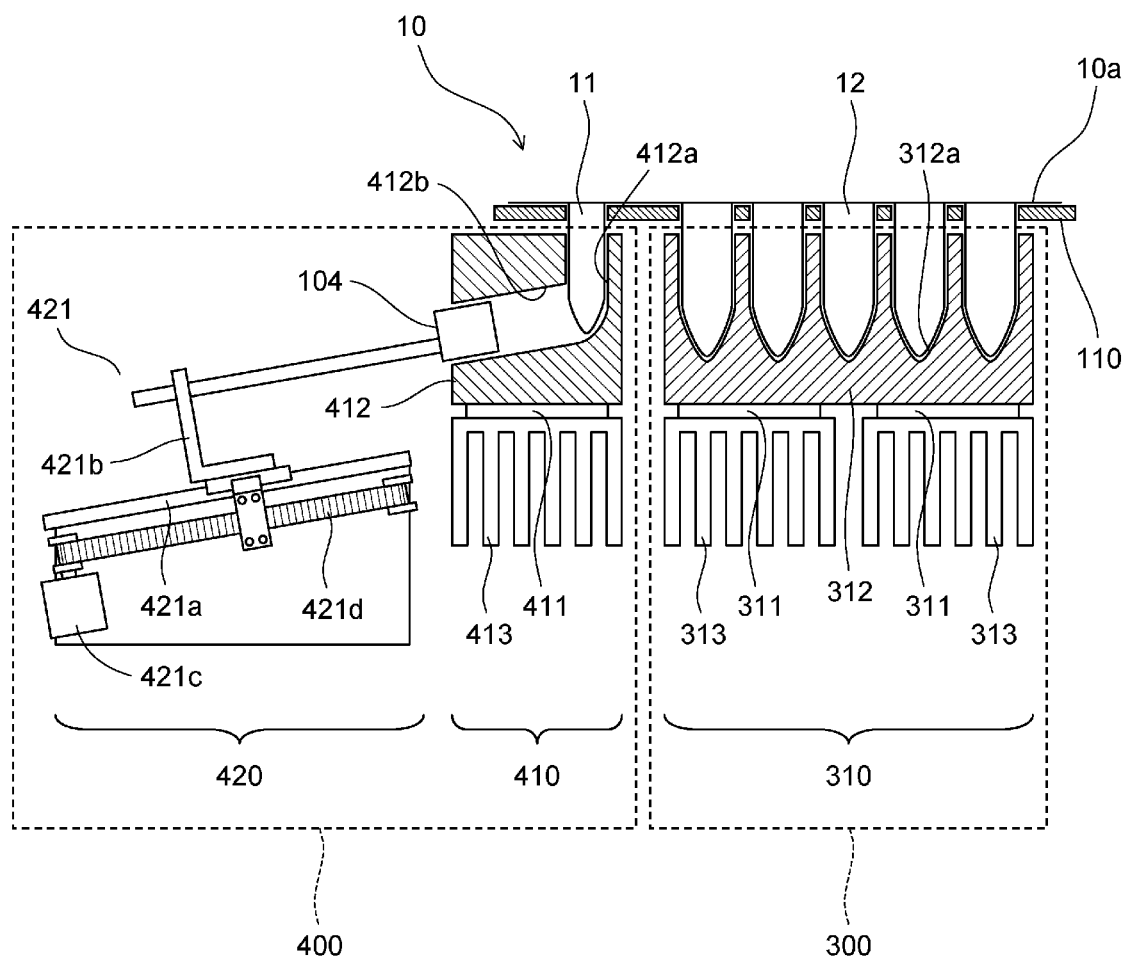
FIG. 14 is a diagram illustrating the configurations of a reaction part and an elution part according to Embodiment 1.

Next, the configurations of the reaction part 300 and the elution part 400 are described with reference to FIG. 14. FIG. 14 illustrates sections of the processing cartridge 10, the plate member 110, and conductive members 312 and 412, and the sections being taken along a plane parallel to the YZ plane passing through the center position of the processing cartridge 10 in terms of the X-axis direction. For the other configurations, outer appearances seen in the X-axis negative direction are illustrated for convenience reasons.

The reaction part 300 includes a heating section 310 that heats the containers 12. The heating section 310 includes two heaters 311, the conductive member 312, and two heat dissipation members 313. The two heaters 311 are placed on the lower surface of the conductive member 312, and heat the five containers 12 by heating the conductive member 312.

The conductive member 312 is made of a metal with high thermal conductivity, and transmits the heat from the heaters 311 to the containers 12. The two heat dissipation members 313 are placed on the lower surfaces of the respective two heaters 311, and after the heaters 311 finish heating, efficiently dissipate the heat in the heaters 311 and the conductive member 312. The conductive member 312 includes five holders 312a for holding the respective five containers 12. The five holders 312a are each formed in a circular hole shape recessed from the upper surface of the conductive member 312. The holder 312a has almost the same diameter as the container 12. The inner surface of each holder 312a is so shaped as to allow the outer surface of the container 12 to be fitted therein.

The elution part 400 includes a heating section 410 that heats the container 11 and a magnetic force application part 420 that applies magnetic force to the container 11. The heating section 410 includes a heater 411, the conductive member 412, and a heat dissipation member 413. The heater 411 is placed on the lower surface of the conductive member 412, and heats the conductive member 412.

The conductive member 412 is made of a metal with high thermal conductivity, and transmits the heat from the heater 411 to the container 11. The heat dissipation member 413 is placed on the lower surface of the heater 411, and after the heater 411 finishes heating, efficiently dissipates the heat in the heater 411 and the conductive member 412. The conductive member 412 includes a holder 412a for holding the container 11 and a hole 412b connecting to the holder 412a. The holder 412a is formed in a circular hole shape recessed from the upper surface of the conductive member 412. The holder 412a has almost the same diameter as the container 11. The inner surface of the holder 412a is so shaped as to allow the outer surface of the container 11 to be fitted therein. The hole 412b extends from the side surface of the conductive member 412 and is connected to the holder 412a.

The magnetic force application part 420 includes the magnet 104 and a magnet driver 421 that moves the magnet 104. The magnet 104 is a permanent magnet. The magnet 104 may be an electromagnet. The magnet driver 421 includes a rail 421a, a movable member 421b, a motor 421c, and a belt 421d. The movable member 421b is so configured as to be movable along the rail 421a. The magnet 104 is set on the movable member 421b via a bar member. The motor 421c is fixed inside the sample processing apparatus 100. The belt 421d runs over two pulleys. The pulley on the Y-axis positive side is connected to the driving shaft of the motor 421c. The movable member 421b is connected to the belt 421d with a fastening fixture.

When the processing cartridge 10 is set, the container 11 is held by the holder 412a as illustrated in FIG. 14. When the motor 421c is driven in this state, the magnet 104 is moved, via the movable member 421b and the belt 421d, along the hole 412b between the outer surface of the container 11 and a position away from the outer surface of the container 11.

To set the processing cartridge 10, the five containers 12 set in the holes 112 of the plate member 110 illustrated in FIG. 11 are inserted into the holders 312a and held by the holders 312a. Meanwhile, the container 11 set in the hole 111 of the plate member 110 illustrated in FIG. 11 is inserted into the holder 412a and held by the holder 412a. In this way, the five containers 12 are placed in the reaction part 300, and the container 11 is placed in the elution part 400.

In Embodiment 1, the reaction part 300 and the elution part 400 are provided for each processing cartridge 10 set for a given plasma sample, i.e., for each of the rows L1 to L6. Thereby, processing involving the reaction part 300 and processing involving the elution part 400 can be performed for each plasma sample independently.

If plasma sample processing is to be performed in synchronization in all the rows L1 to L6, one reaction part 300 and one elution part 400 may be shared by the rows L1 to L6. In this case, in order for the one reaction part 300 and the one elution part 400 to support the six processing cartridges 10 placed on the rows L1 to L6, the heaters 311 and 411, the conductive members 312 and 412, and the heat dissipation members 313 and 413 are extended in the X-axis direction. Further, six magnets 104 corresponding to the respective containers 11 are driven by one magnet driver 421.

As illustrated in FIG. 15, the sample processing apparatus 100 includes the controller 601, a memory or a storage part 602, a display part 603, an input part 604, a driver part 605, a sensor part 606, the dispensing part 200, the reaction parts 300, the elution parts 400, and the cooling parts 500.

The controller 601 is configured with a CPU or a microcomputer. Based on programs stored in the memory or storage part 602, the controller 601 receives signals from the parts in the sample processing apparatus 100 and controls the parts in the sample processing apparatus 100. The memory or storage part 602 is configured with a RAM, a ROM, a hard disk, and/or the like. The controller 601 may be configured with a CPU and a microcomputer. Then, for example, the microcomputer may control the units in the sample processing apparatus 100, and the CPU communicatively connected to the microcomputer may transmit command signals to the microcomputer. In other words, the controller 601 may be configured with a plurality of controllers.

The display part 603 is configured with a display. The input part 604 may be configured with a mouse, a keyboard, a touch panel, and/or the like. Instead of the display part 603 and the input part 604, the sample processing apparatus 100 may include a display/input unit configured with a touch panel display. The driver part 605 includes other mechanisms provided in the sample processing apparatus 100. The sensor part 606 includes other sensors provided in the sample processing apparatus 100.

Next, an outline of the procedure of processing performed by the sample processing apparatus 100 is described with reference to FIGS. 11 and 16A to 16F.

An operator sets the sample container 51 housing a plasma sample in the holder 151. FIG. 11 illustrates an example where the sample containers 51 are set in the right three holders 151 corresponding to the rows L1 to L3 out of the six holders 151 to process three plasma samples.

Using the input part 604, the operator inputs for each of the sample containers 51 the amount of plasma sample to be processed. More specifically, using the input part 604, the operator inputs a value 1 mL, 2 mL, 3 mL, 4 mL, or 5 mL for each plasma sample according to the amount of the plasma sample housed in the sample container 51. Using the input part 604, the operator then inputs an instruction to start processing.

Once the instruction to start is input, the controller 601 performs processing of the plasma samples housed in the respective sample containers 51 at the same time. The processing of a plasma sample housed in a given sample container 51 uses the processing cartridge 10, the reagent cartridge 30, the reagent container 41, the pipette tips 21 and 22, and the container 61, all in line with the given sample container 51 in the Y-axis direction.

The controller 601 controls the dispensing part 200 so that the plasma sample housed in the sample container 51, reagent housed in the reagent cartridge 30, and reagent housed in the reagent container 41 are dispensed to the container(s) 12: the number of the containers 12 here is determined based on the amount of plasma sample inputted. More specifically, when 1 mL, 2 mL, 3 mL, 4 mL, or 5 mL is inputted as the amount of plasma sample to be processed, the plasma sample and the reagent are dispensed into one, two, three, four, or five containers 12, respectively.

For example, for a plasma sample for which 5 mL is inputted as the amount to be processed, the plasma sample and the reagent are dispensed into five containers 12 arranged in the same row as the plasma sample. For a plasma sample for which 3 mL is inputted as the amount to be processed, the plasma sample and the reagent are dispensed into three containers 12 arranged in the same row as the plasma sample. For convenience reasons, the following describes plasma sample processing where 5 ml is inputted as the amount to be processed. The following dispensing processing is performed by the controller 601 controlling the dispensing part 200.

Figure 16A:
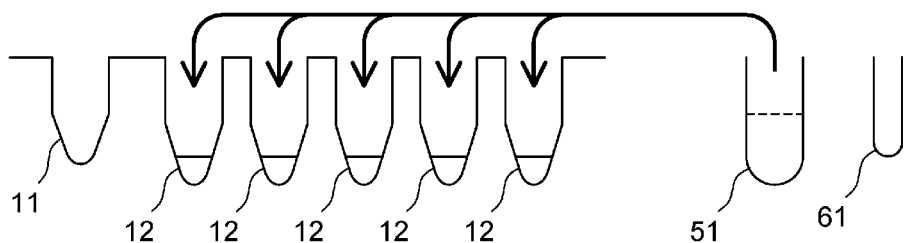
FIGS. 16A to 16F are diagrams illustrating a procedure of the processing performed by a sample processing apparatus according to Embodiment 1.

First, Proteinase K housed in the reagent container 41 is dispensed to five containers 12. Equal amounts of Proteinase K are dispensed to the containers 12. Next, as illustrated in FIG. 16A, the plasma sample housed in the sample container 51 is dispensed to the five containers 12. To each container 12, 1 mL of plasma sample is dispensed.

Figure 16B:
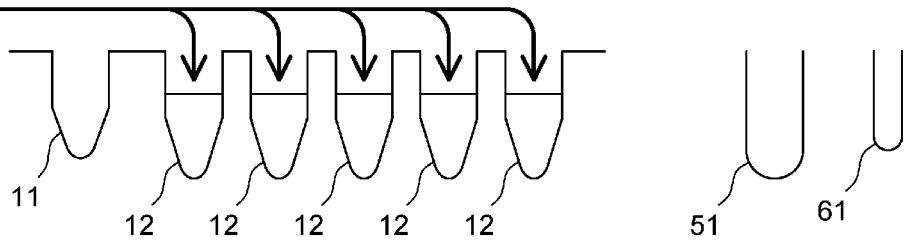

Next, as illustrated in FIG. 16B, solubilizing liquid, preparation liquid, extraction liquid, and magnetic-particle suspended reagent housed in the reagent cartridge 30 are dispensed to the five containers 12. Equal amounts of each reagent are dispensed to the respective five containers 12, causing DNA in the plasma sample to be adhered to the magnetic particles.

Figure 16C:
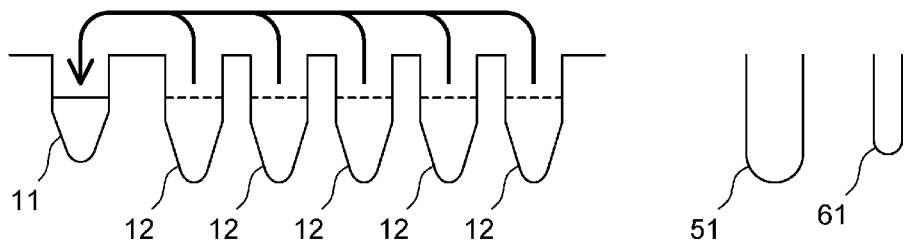
Figure 16D:
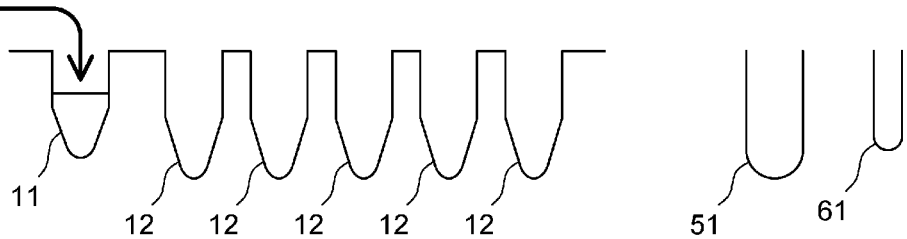

Next, as illustrated in FIG. 16C, a predetermined quantity of a specimen is dispensed from each container 12 to the container 11 sequentially, and impurities in the specimen are removed as a liquid component. After the specimens in all the containers 12 are dispensed to the container 11, as illustrated in FIG. 16D, the first to third cleaning liquids housed in the reagent cartridge 30 are dispensed to the container 11, and impurities in the specimen in the container 11 are removed as a liquid component.

Figure 16E:
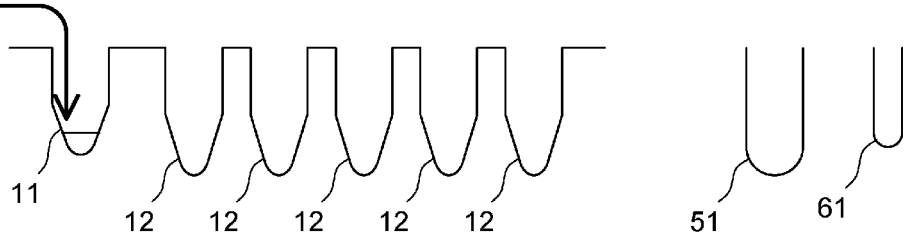
Figure 16F:
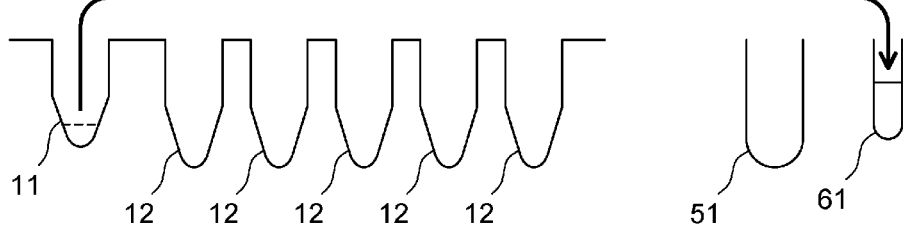

Next, as illustrated in FIG. 16E, elution liquid housed in the reagent cartridge 30 is dispensed to the container 11, separating the DNA and the magnetic particles from each other. Next, with magnetic force applied to the container 11, the liquid in the container 11 is dispensed to the container 61, as illustrated in FIG. 16F. The liquid moved to the container 61 contains extracted DNA. Thus, processing for one plasma sample is completed.

When an amount other than 5 mL is inputted as the amount of plasma sample to be processed, the number of containers used for the processing is changed depending on the amount of plasma sample inputted. For example, if 3 mL is inputted as the amount of plasma sample to be processed, 1 mL of plasma sample is dispensed to each of three containers 12.

In this way, a plasma sample and reagent are dispensed to the containers 12 whose number to be used is determined according to the amount of plasma sample, and in the containers 12 to which the plasma sample and reagent have been dispensed, reactions between the reagent and the plasma sample occur at the same time. This shortens the time it takes for the plasma sample to react with the reagent, compared to a condition in which the plasma sample to be processed and the reagent are dispensed collectively to one large-capacity container. Further, in a condition in which a reaction occurs in a large-capacity container, the reaction may vary in its extent of reaction depending on the amount of plasma sample, and therefore stable DNA extraction is difficult. By contrast, in a condition in which reactions occur in the containers 12 whose number being used is determined according to the amount of plasma sample as described above, stable DNA extraction can be achieved irrespective of the amount of plasma sample.

Next, with reference to FIGS. 17A to 17F, a description is given of how DNA is extracted from a plasma sample through reactions in the containers. Note that in FIGS. 17A to 17F, the liquid level in each container is at the same position, and the containers 11, 12, 51, and 61 have the same size, for convenience reasons.

Figure 17A:
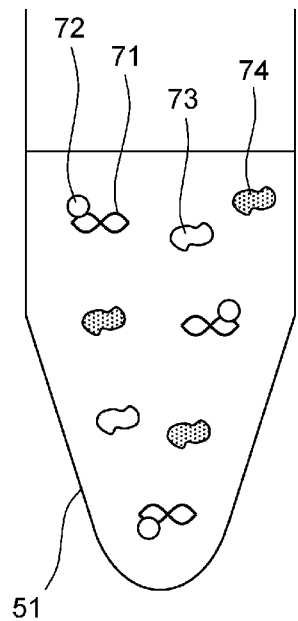
FIGS. 17A to 17F are diagrams illustrating how DNA is extracted from a plasma sample by the processing performed by a sample processing apparatus according to Embodiment 1.

As illustrated in FIG. 17A, a plasma sample in the sample container 51 contains DNA 71, histone 72 which is DNA-binding protein that binds with DNA in a plasma sample, enzyme 73 that decomposes DNA 71, protein 74 in the plasma sample, and the like. The DNA 71 in the plasma sample is cell-free DNA. Proteinase K is dispensed to the container 12, a plasma sample is dispensed to the container 12, and solubilizing liquid is dispensed to the container 12. Then, the Proteinase K decomposes the histone 72 bound with the DNA 71, separating the histone 72 from the DNA 71. In addition, the Proteinase K decomposes the enzyme 73 and inhibits the function of the enzyme 73. In addition, the Proteinase K decomposes the protein 74 in the plasma sample. The solubilizing liquid creates an environment that makes it easy for the Proteinase K to function.

Next, preparation liquid and extraction liquid are dispensed to the container 12. Being highly hydrophilic, the DNA 71 easily binds with water molecules in solution by hydrogen bonding. By contrast, silica covering the surfaces of magnetic particles 77 illustrated in FIG. 17C is highly hydrophobic. Thus, the DNA 71 in the initial state does not easily bind with silica on the magnetic particles 77. The preparation liquid removes hydrated molecules from the DNA 71 and makes the DNA 71 hydrophobic. Then, the DNA 71, now hydrophobic, is adhered to the silica on the magnetic particles 77. In addition, the elution liquid creates an environment for causing the DNA 71 to be adhered to the magnetic particles 77. When a reaction in the container 12 progresses, the inside of the container 12 is in, for example, a state illustrated in FIG. 17B.

Figure 17B:
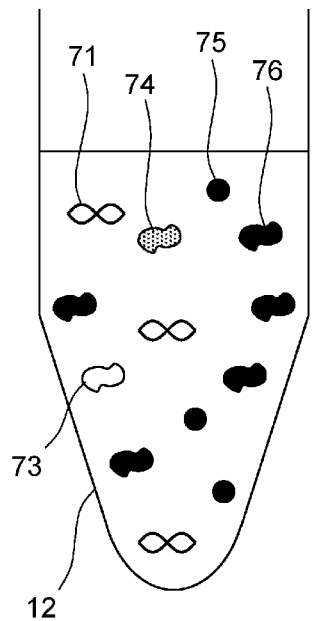
Figure 17C:
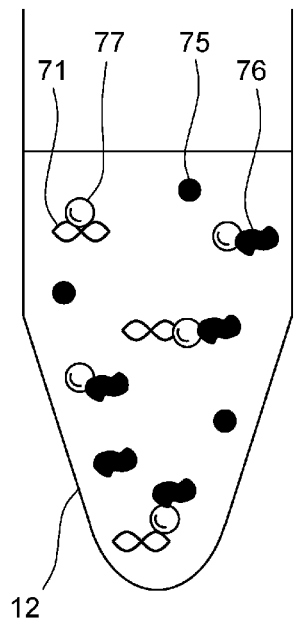
Figure 17D:
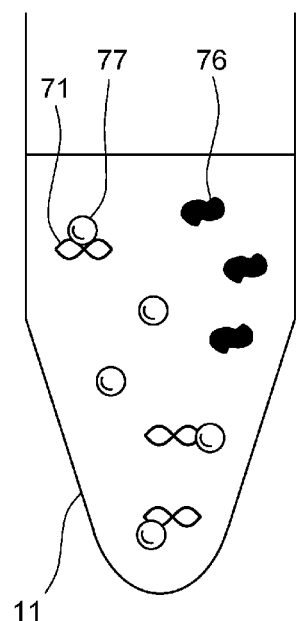
Figure 17E:
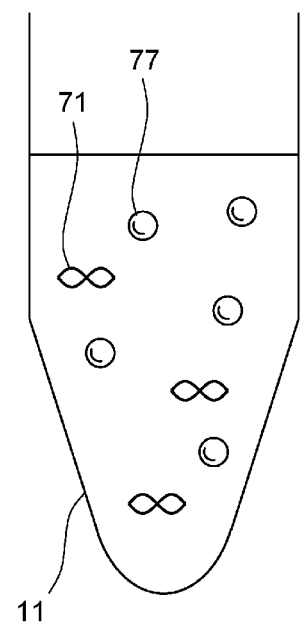
Figure 17F:
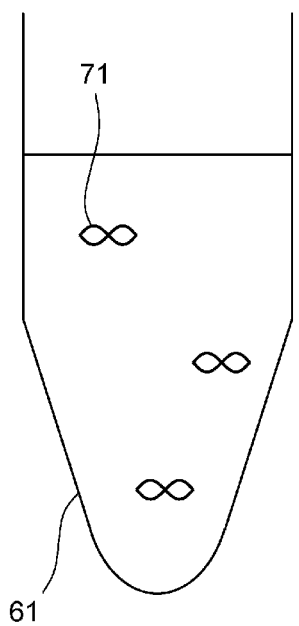

As illustrated in FIG. 17B, the specimen in the container 12 in this state contains the DNA 71, the enzyme 73, the protein 74 in the plasma sample, altered substances 75 and 76, and the like. The altered substances 75 are the altered and decomposed histone 72. The altered substances 76 are the altered and decomposed enzyme 73 and protein 74 in the plasma sample. When the reaction in the container 12 progresses, the histone 72 is separated from the DNA 71, and the histone 72, the enzyme 73, and the protein 74 in the plasma sample are altered and decomposed. Further, magnetic-particle suspended reagent is dispensed to the container 12. Then, the DNA 71 is adhered to the magnetic particles 77, and the inside of the container 12 is in, for example, a state illustrated in FIG. 17C. Note that some altered substances 75 and 76 in the plasma sample are also adhered to the magnetic particles 77.

Next, the specimen in the container 12 is dispensed to the container 11, and the magnet 104 of the elution part 400 causes the magnetic particles 77 to adhere to the inner wall 11a of the container 11. Then, the supernatant is removed from the container 11. Thereby, the altered substances 75 and 76 not bound with the magnetic particles 77 in the plasma sample are removed.

Next, the first cleaning liquid is dispensed to the container 11. This separates the altered substances 75 and 76 bound with the magnetic particles 77, bringing the inside of the container 11 into, for example, a state illustrated in FIG. 17D. Then, the magnet 104 is used to remove the supernatant from the container 11, thereby removing some of the altered substances 75 and 76 from the specimen. Next, the second cleaning liquid is dispensed to the container 11. Then, the magnet 104 is used to remove the supernatant from the container 11, thereby further removing the altered substances 75 and 76 from the specimen. Next, the third cleaning liquid is dispensed to the container 11. Then, the magnet 104 is used to remove supernatant from the container 11, thereby further removing the altered substances 75 and 76 from the specimen.

Next, elution liquid is dispensed to the container 11. This releases the DNA 71 from the magnetic particles 77, bringing the inside of the container 11 to, for example, a state illustrated in FIG. 17E. Next, while the magnet 104 is causing the magnetic particles 77 to adhere to the inner wall of the container 11, the liquid in the container 11 is dispensed to the container 61. In this state, the liquid in the container 61 is in, for example, a state illustrated in FIG. 17F, where unnecessary substances other than the DNA 71 have been removed. With this, nucleic acid extraction processing for one plasma sample ends.

Next, with reference to the flowcharts illustrated in FIGS. 18 to 22A, a description is given of the processing performed by the sample processing apparatus 100. The following flowcharts are performed for each plasma sample set in one of the rows L1 to L6. In addition, the steps of the following flowcharts are executed when the controller 601 controls the dispensing part 200, the reaction part 300, and the elution part 400.

Figure 18:
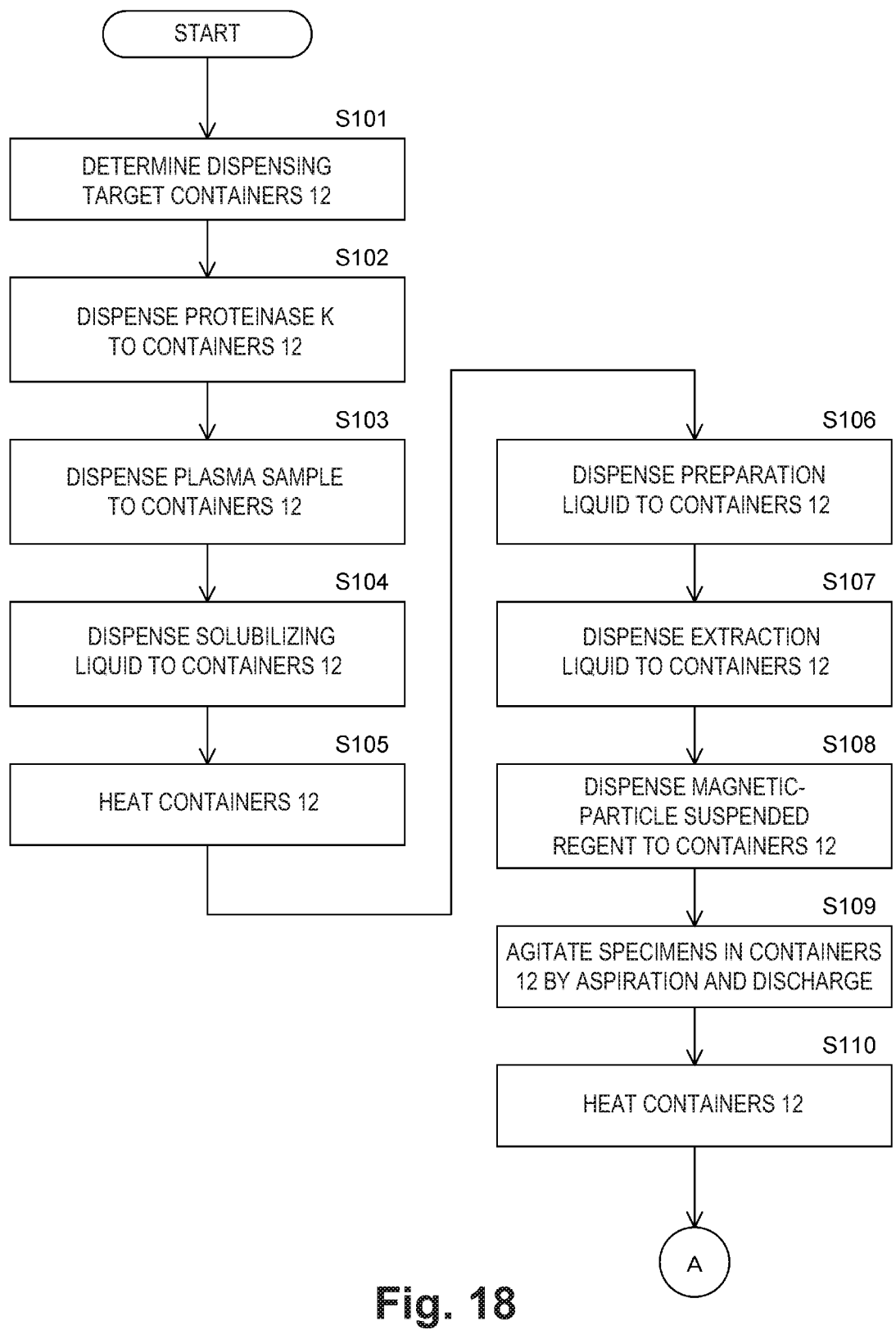
FIG. 18 is a flowchart illustrating processing performed by a sample processing apparatus according to Embodiment 1.

As illustrated in FIG. 18, in Step S101, the controller 601 reads information on the plasma sample amount for the plasma sample to be processed from the memory or storage part 602, and according to the information on the plasma sample amount thus read, determines dispensing target containers 12. More specifically, if the information on the plasma sample amount indicates 1 mL, 2 mL, 3 mL, 4 mL, or 5 mL, the number of dispensing target containers 12 is one, two, three, four, or five, respectively. Dispensing processing on the containers 12 is performed only on the dispensing target containers 12.

In Step S102, the controller 601 attaches a new pipette tip 21 held in the holder member 120 to the nozzle 201, and dispenses a predetermined amount of Proteinase K housed in the reagent container 41 to each of the containers 12. In Step S103, the controller 601 discards the pipette tip 21 attached to the nozzle 201, attaches a new pipette tip 21 to the nozzle 201, and dispenses 1 mL of a plasma sample housed in the sample container 51 to each of the containers 12.

In Step S104, the controller 601 discards the pipette tip 21 attached to the nozzle 201, attaches a new pipette tip 21 to the nozzle 201, and dispenses a predetermined amount of solubilizing liquid housed in the reagent cartridge 30 to each of the containers 12. In Step S105, the controller 601 heats the containers 12 with the heaters 311 of the reaction part 300 to heat the specimen in each container 12. This promotes the reactions in the containers 12, separating the histone 72 from the DNA 71 and altering and decomposing the histone 72, the enzyme 73, and the protein 74 in the plasma sample as described with reference to FIG. 17B.

In Step S106, the controller 601 discards the pipette tip 21 attached to the nozzle 201, attaches a new pipette tip 21 to the nozzle 201, and dispenses a predetermined amount of preparation liquid housed in the reagent cartridge 30 to each of the containers 12. Further, in Step S107, the controller 601 dispenses a predetermined amount of extraction liquid housed in the reagent cartridge 30 to each container 12.

In Step S108, the controller 601 discards the pipette tip 21 attached to the nozzle 201, attaches a new pipette tip 22 to the nozzle 202, and dispenses a predetermined amount of magnetic-particle suspended reagent housed in the reagent cartridge 30 to each container 12. In Step S109, the controller 601 agitates the specimen in each container 12 by repeating an operation of aspirating and discharging the sample in the container 12 inside the container 12. This agitation operation is called "agitation by aspiration and discharge" hereinbelow. In Step S110, the controller 601 heats the containers 12 with the heaters 311 to heat the specimens in the containers 12. Thereby, the DNA 71 is adhered to the magnetic particles 77 as described with reference to FIG. 17C. The processing then proceeds to Step S201 in FIG. 19.

Figure 19:
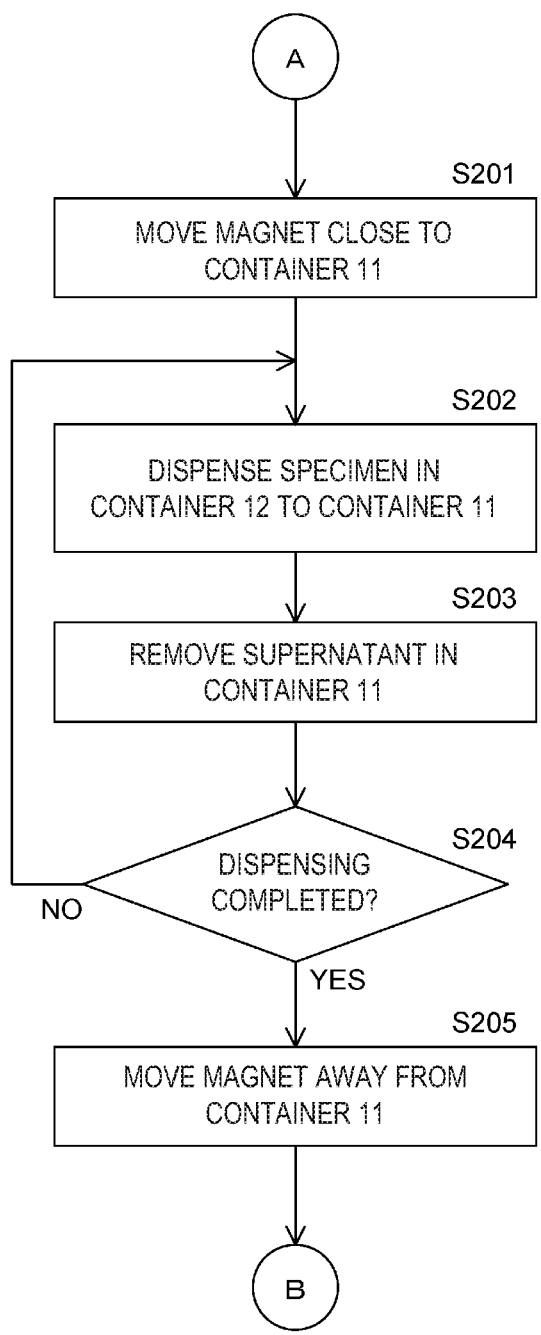
FIG. 19 is a flowchart illustrating processing performed by a sample processing apparatus according to Embodiment 1.

As illustrated in FIG. 19, in Step S201, the controller 601 moves the magnet 104 of the elution part 400 close to the container 11. Then, the controller 601 discards the pipette tip 22 attached to the nozzle 202 and attaches a new pipette tip 21 to the nozzle 201.

Next, in Step S202, the controller 601 dispenses 1.2 mL of the specimen in the container(s) 12 to the container 11. In this event, if the targeted container 12 contains 1.2 mL or more of specimen, the specimen is dispensed from this container 12 to the container 11. If the targeted container 12 does not contain 1.2 mL or more of specimen, and if there is other container 12 from which a specimen has not been dispensed in Step S202, the entire specimen in the targeted container 12 is dispensed to the other container 12 yet to have the specimen dispensed therefrom, and 1.2 mL of specimen is dispensed from the other container 12 to the container 11. If the targeted container 12 does not contain 1.2 mL or more of specimen, and if there is no container 12 from which a specimen has not been dispensed in Step S202, the entire specimen in the targeted container 12 is dispensed to the container 11.

In Step S203, the controller 601 aspirates the supernatant in the container 11 and discards it to the discarding part. More specifically, the liquid component in the container 11 is aspirated and discarded. In Step S204, the controller 601 determines whether the entire specimen in every container 12 has been dispensed to the container 11. If the entire specimen in every container 12 has not been dispensed to the container 11, the controller 601 returns the processing to Step S202. If the entire specimen in every container 12 has been dispensed to the container 11, the controller 601 causes the processing to proceed to Step S205.

In this way, in the processing in Steps S202 to S204, a certain quantity of the specimen is dispensed from the containers 12 to the container 11, and the supernatant is removed from the container 11 with the magnetic particles adhering to the inner wall 11a of the container 11, and these operations are repeated a plurality of times. This enables the supernatant containing unwanted components to be removed speedily and surely, compared to a case where the specimens in the containers 12 are collectively transferred to a large-capacity container, and the supernatant removal operation is performed only once in this container.

In Step S205, the controller 601 moves the magnet 104 of the elution part 400 away from the container 11. Next, the processing proceeds to Step S301 in FIG. 20.

Figure 20:
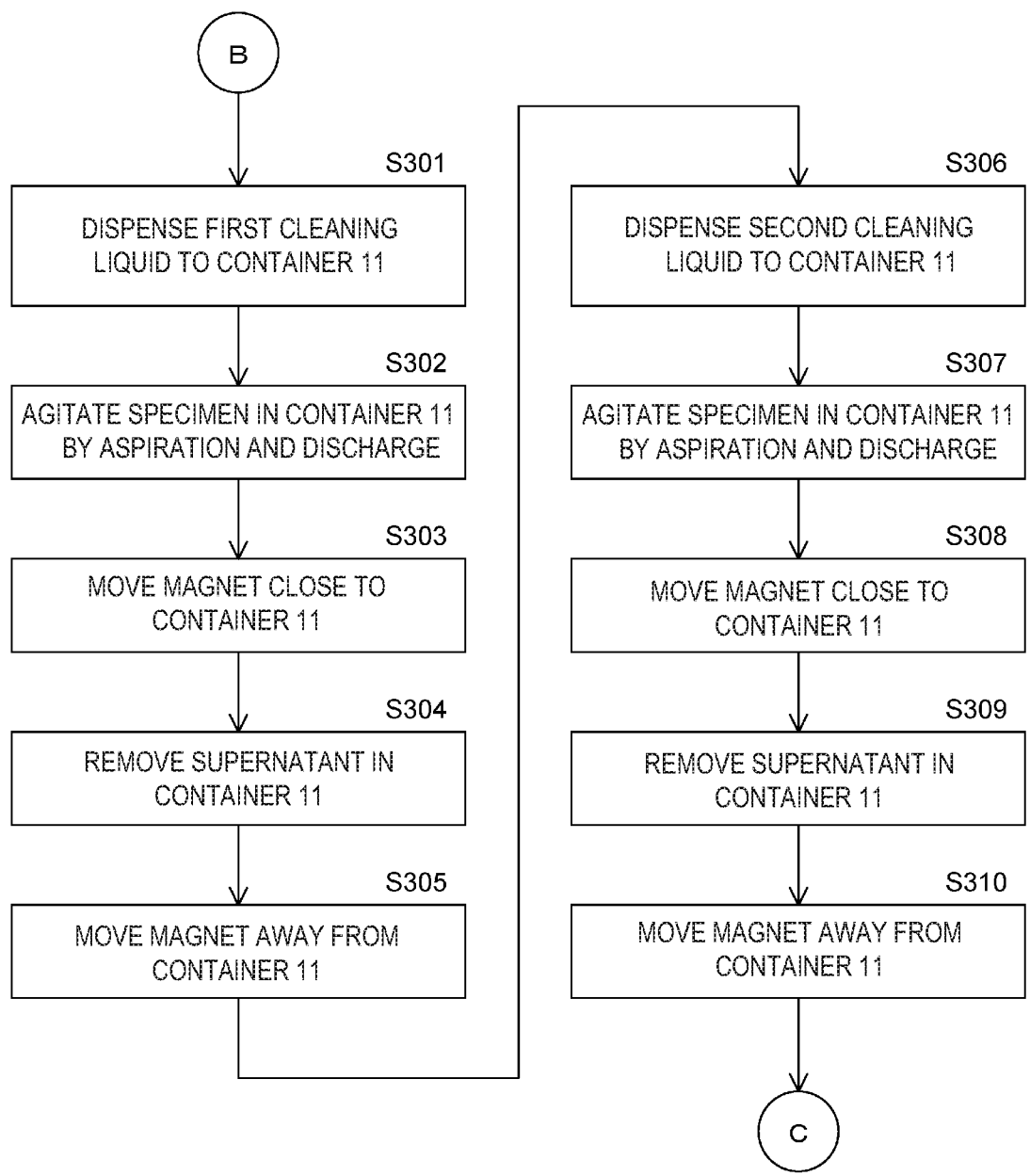
FIG. 20 is a flowchart illustrating processing performed by a sample processing apparatus according to Embodiment 1.

As illustrated in FIG. 20, in Step S301, the controller 601 discards the pipette tip 21 attached to the nozzle 201, attaches a new pipette tip 21 to the nozzle 201, and dispenses 600 μL of the first cleaning liquid housed in the reagent cartridge 30 to the container 11. In Step S302, the controller 601 agitates the specimen in the container 11 by aspiration and discharge. In Step S303, the controller 601 moves the magnet 104 of the elution part 400 close to the container 11. As a result, the magnetic particles 77 in the specimen adhere to the inner wall 11a of the container 11. In Step S304, the controller 601 removes the supernatant in the container 11. More specifically, the liquid component in the container 11 is aspirated and discarded. With this, cleaning with the first cleaning liquid is completed. In Step S305, the controller 601 moves the magnet 104 away from the container 11.

In Step S306, the controller 601 dispenses 750 μL of the second cleaning liquid housed in the reagent cartridge 30 to the container 11. The controller 601 then performs the processing from Steps S307 to S310 in the same manner as the processing from Steps S302 to S305. After the supernatant is removed in Step S309, cleaning with the second cleaning liquid is completed. When the first cleaning liquid and the second cleaning liquid are dispensed, the altered substances 75 and 76 bound with the magnetic particles 77 are separated therefrom, as described with reference to FIG. 17D. Then, when the supernatants are removed in Steps S304 and S309, the altered substances 75 and 76 are removed from the specimen. Next, the processing proceeds to Step S401 in FIG. 21.

Figure 21:
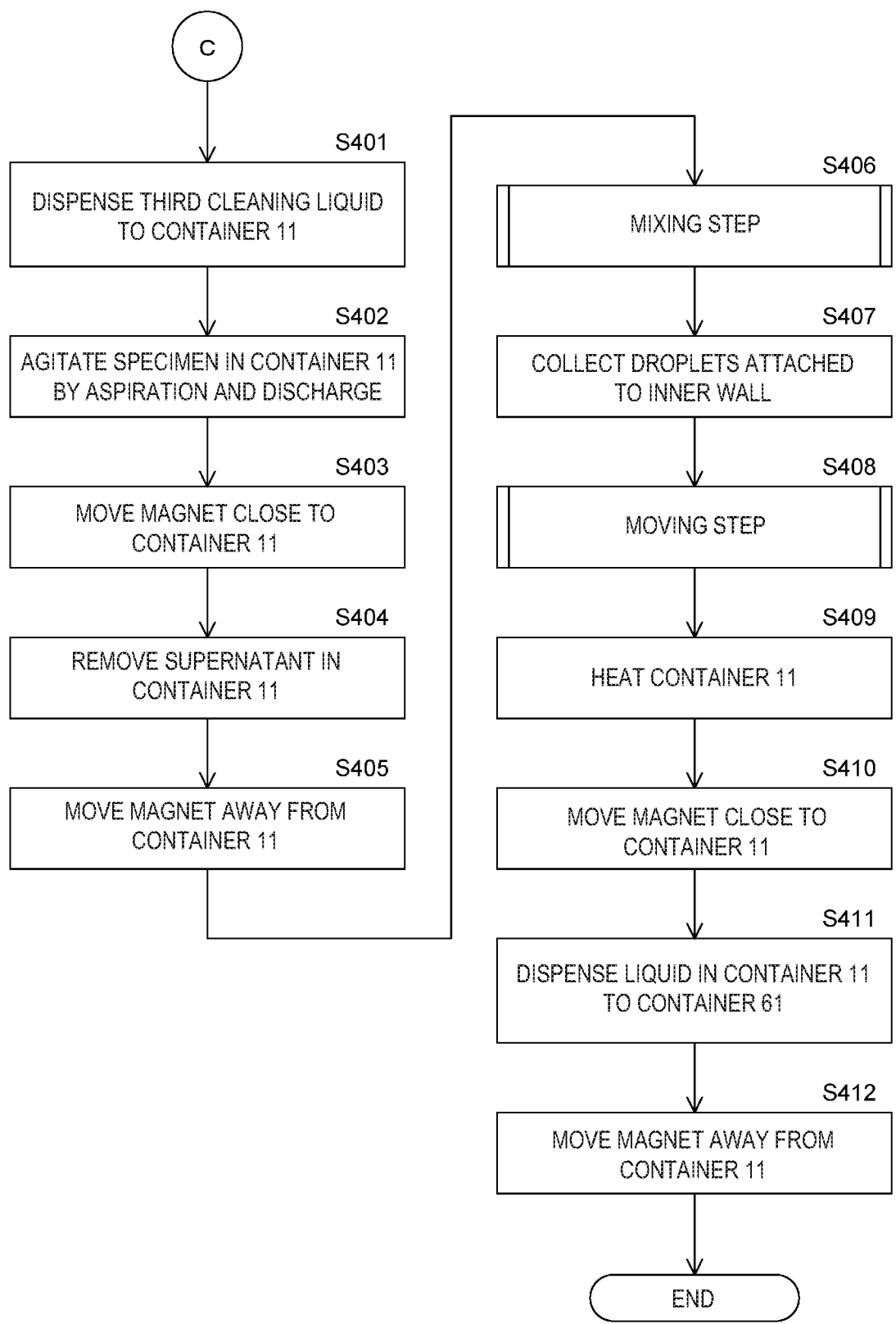
FIG. 21 is a flowchart illustrating processing performed by a sample processing apparatus according to Embodiment 1.

As illustrated in FIG. 21, in Step S401 the controller 601 dispenses 750 μL of the third cleaning liquid housed in the reagent cartridge 30 to the container 11. In this event, the liquid level of the third cleaning liquid is located higher than the upper edge of the attachment area 11c to which the magnetic particles adhere, as illustrated in FIG. 4A. In Step S402, the controller 601 agitates the third cleaning liquid in the container 11 by aspiration and discharge.

The state of the container 11 after the processing in Step S402 is ended corresponds to the state immediately before Step S1 in FIG. 1 is started. Thus, the suspension illustrated in FIG. 4A corresponds to the third cleaning liquid for cleaning magnetic particles. The subsequent processing from Steps S403 to S408 corresponds to the processing from Steps S1 to S6 in FIG. 1.

In Step S403, the controller 601 moves the magnet 104 of the elution part 400 close to the magnet 104. This causes magnetic particles contained in the third cleaning liquid to adhere to the attachment area 11c on the inner wall 11a, as illustrated in FIG. 4A. In Step S404, the controller 601 removes the supernatant in the container 11. More specifically, as illustrated in FIG. 4B, the liquid component in the container 11 is aspirated and discarded. With this, cleaning with the third cleaning liquid is completed. When the supernatant is removed in Step S404, the altered substances 75 and 76 are removed from the specimen. In Step S405, the controller 601 moves the magnet 104 away from the container 11.

Figure 22A:
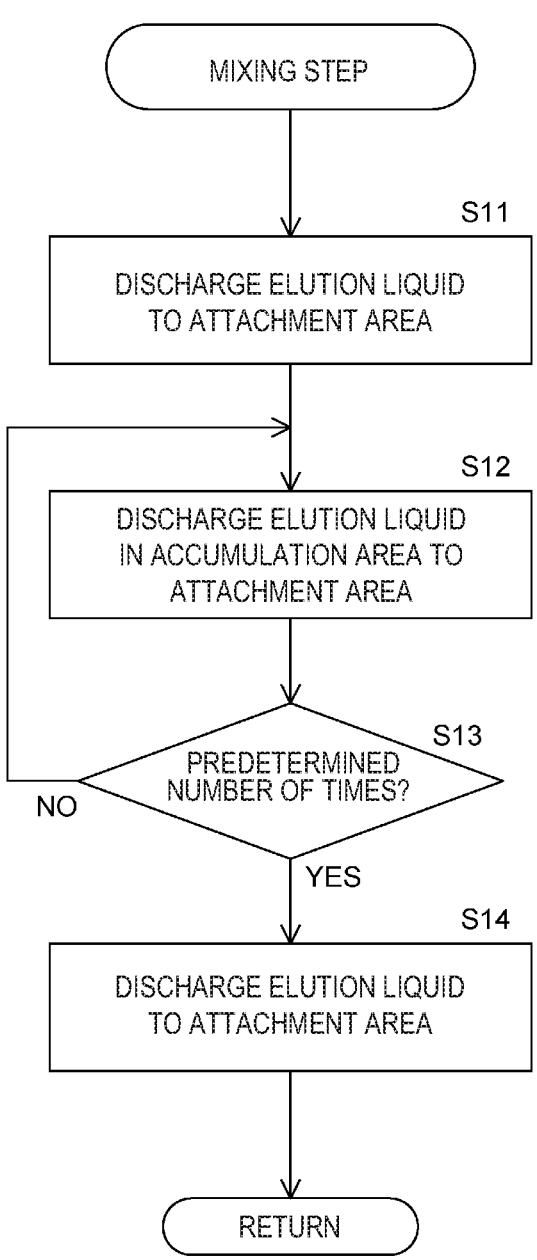
FIG. 22A is a flowchart illustrating a mixing step performed by a sample processing apparatus according to Embodiment 1.

In Step S406, the controller 601 discards the pipette tip 21 attached to the nozzle 201, attaches a new pipette tip 22 to the nozzle 202, and performs the mixing step illustrated in FIG. 22A.

The mixing step performed by the sample processing apparatus 100 as illustrated in FIG. 22A is different from that in FIG. 2A in that Step S14 is added after Step S13. In Step S11, the controller 601, as described using FIG. 4D, discharges 110 µL of elution liquid housed in the reagent cartridge 30 to the attachment area 11c. Then, the liquid level of the elution liquid is, as in the state illustrated in FIG. 4D, located lower than the upper edge of the attachment area 11c to which the magnetic particles adhere.

In Step S12, the controller 601 performs the operation of discharging the elution liquid in the accumulation area 11d to the attachment area 11c as described using FIGS. 4E and 4F. In Step S12 in this case, the controller 601 aspirates 95 µL of the elution liquid in the container 11, and discharge 85 µL of the 95 µL of elution liquid thus aspirated, to the container 11. This way, mixing of the magnetic particles and the elution liquid can be promoted while generation of air bubbles in the pipette tip 22 and in the container 11 is prevented. In Step S13, the controller 601 determines whether the processing in Step S12 has been performed a predetermined number of times. If the processing in Step S12 has not been performed a predetermined number of times, the processing returns to Step S12 to repeat the processing of Step S12.

After the processing of Step S12 is performed a predetermined number of times, in Step S14, the controller 601 discharges 30 µL of the elution liquid housed in the reagent cartridge 30 to the attachment area 11c. More specifically, after the processing of Step S12, i.e., discharge of the elution liquid accumulated in the accumulation area 11d toward the attachment area 11c, is finished, a new elution liquid which is different from the elution liquid accumulated in the accumulation area 11d and contains no magnetic particle is discharged to the attachment area 11c. This makes it difficult for elution liquid droplets containing magnetic particles to remain on the inner wall 11a of the container 11, and therefore can increase the number of magnetic particles contained in the accumulation area 11d. With this, the mixing step performed by the sample processing apparatus 100 is ended.

Referring back to FIG. 21, in Step S407, the controller 601 collects droplets attached to the inner wall 11a as described with reference to FIGS. 5D to 7C.

Figure 22B:
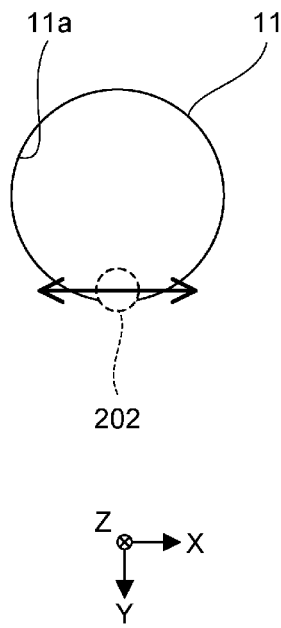
FIG. 22B is a diagram illustrating the movement of a nozzle of a sample processing apparatus according to Embodiment 1.

In Step S407, with the pipette tip 22 touching the inner wall 11a of the container 11, the controller 601 moves the nozzle 202 having the pipette tip 22 attached thereto in a direction orthogonal to the center axis of the container 11. The center axis of the container 11 is parallel to the Z-axis direction. More specifically, the controller 601 moves the nozzle 202 so that the pipette tip 22 attached to the nozzle 202 may touch the inner wall 11a of the container 11 on the Y-axis positive side. The controller 601 then moves the nozzle 202 from this state in the X-axis direction as illustrated in FIG. 22B. This makes pipette tip 22 attached to the nozzle 202 elastically deform and move circumferentially along the inner wall 11a as illustrated in FIGS. 6A to 7C. When the pipette tip 22 is thus moved circumferentially along the inner wall 11a, droplets attached to the inner wall 11a can be collected efficiently. Further, since the nozzle 202 only has to be moved linearly, control of the pipette tip 22 is simple.

Figure 22C:
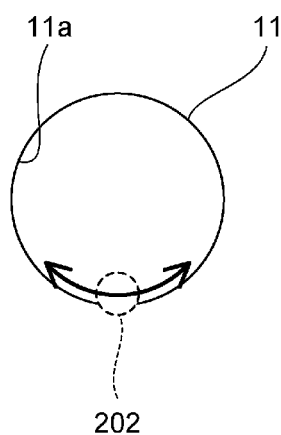
FIG. 22C is a diagram illustrating the movement of a nozzle of a sample processing apparatus according to a modification of Embodiment 1.

Note that, as illustrated in FIG. 22C, the controller 601 may move the nozzle 202 having the pipette tip 22 attached thereto circumferentially along the inner wall 11a of the container 11. Also in this case, the pipette tip 22 is moved circumferentially along the inner wall 11a, and can efficiently collect droplets attached to the inner wall 11a. In addition, elastic deformation of the pipette tip 22 is reduced when the pipette tip 22 is moved, and therefore the attachment state of the pipette tip 22 with respect to the nozzle 202 is maintained stable.

Next, in Step S408, the controller 601 performs the moving step in the same manner as FIG. 2B. In Step S408, the controller 601 moves the nozzle 202 so that the pipette tip 22 moves as illustrated in FIGS. 7D to 10F. Thereby, the droplets collected in Step S407 are moved to the accumulation area 11d.

In Step S409, the controller 601 heats the container 11 with the heater 411 of the elution part 400 to heat the specimen in the container 11. This promotes the reaction in the container 11, releasing the DNA 71 from the magnetic particles 77, as described with reference to FIG. 17E.

Figures 23A, 23B, 23C:
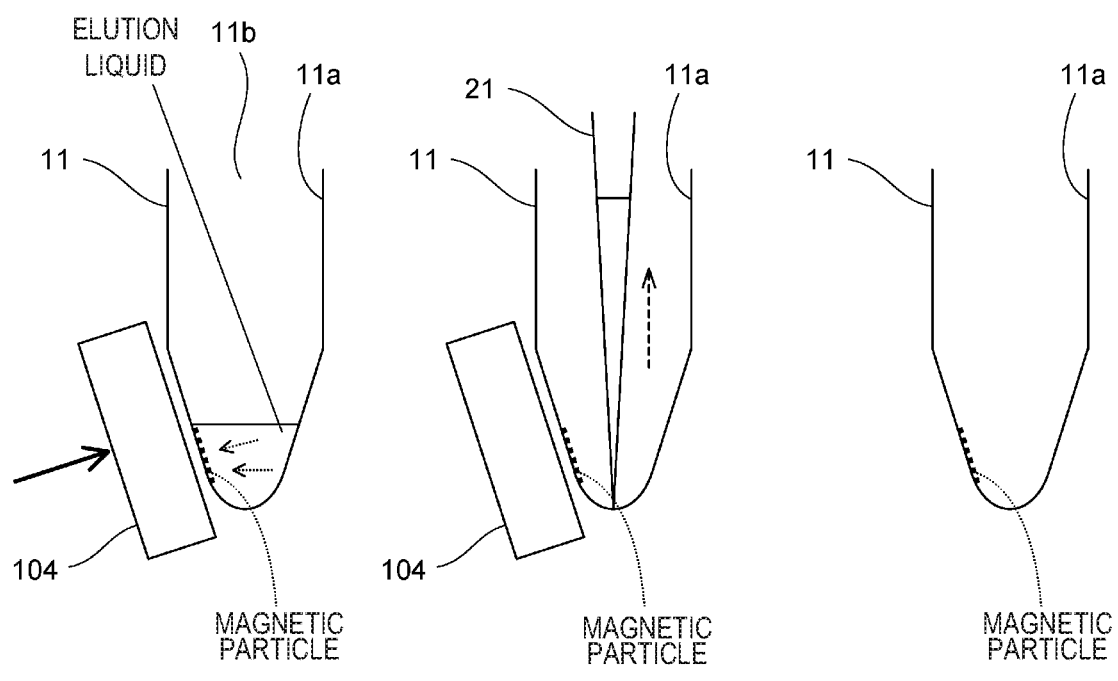
FIGS. 23A to 23C are side views of a container, illustrating processing according to Embodiment 1 to take out liquid in which DNA is released.

In Step S410, the controller 601 moves the magnet 104 close to the container 11 to apply magnetic force to the container 11. Thereby, as illustrated in FIG. 23A, the magnetic particles 77 in the elution liquid adhere to the inner wall 11a of the container 11. In Step S411, the controller 601 dispenses the liquid in the container 11 to the container 61. More specifically, as illustrated in FIG. 23B, with the magnetic particles in the container 11 adhering to the inner wall 11a by the magnet 104, the controller 601 aspirates the liquid in the container 11 with the pipette tip 22. Then, the controller 601 discharges the liquid aspirated into the pipette tip 22 to the container 61. The liquid aspirated from the container 11 and discharged to the container 61 is in a state where unwanted substances other than the DNA 71 have been removed, as described with reference to FIG. 17F.

By thus performing Steps S410 and S411 after the moving step of Step S408 in which the droplets are moved to the accumulation area 11d, DNA contained in the plasma sample can be collected into the container 61.

In Step S412, the controller 601 moves the magnet 104 away from the container 11 as illustrated in FIG. 23C. With this, the processing performed by the sample processing apparatus 100 ends.

Embodiment 2

In Embodiment 1, in the mixing step, the elution liquid is discharged from the pipette tip 22 to the attachment area 11c from near the end portion of the container 11 on the opening 11b side as illustrated in FIG. 4D. However, when the upper edge of the attachment area 11c is lower than that illustrated in FIG. 4D, the elution liquid may be discharged toward the attachment area 11c from the vicinity of the lower portion inside the container 11. In Embodiment 2, the upper edge of the attachment area 11c is located at a low position, and thus the elution liquid is aspirated and discharged as illustrated in FIGS. 24A to 24C in the mixing step.

More specifically, as illustrated in FIG. 24A, the elution liquid is discharged from the vicinity of the lower portion inside the container 11. Next, as illustrated in FIG. 24B, the elution liquid is aspirated by the pipette tip 22 like in Embodiment 1. Then, as illustrated in FIG. 24C, the elution liquid is discharged toward the attachment area 11c again from the vicinity of the lower portion inside the container 11.

Figures 25A, 25B, 25C:
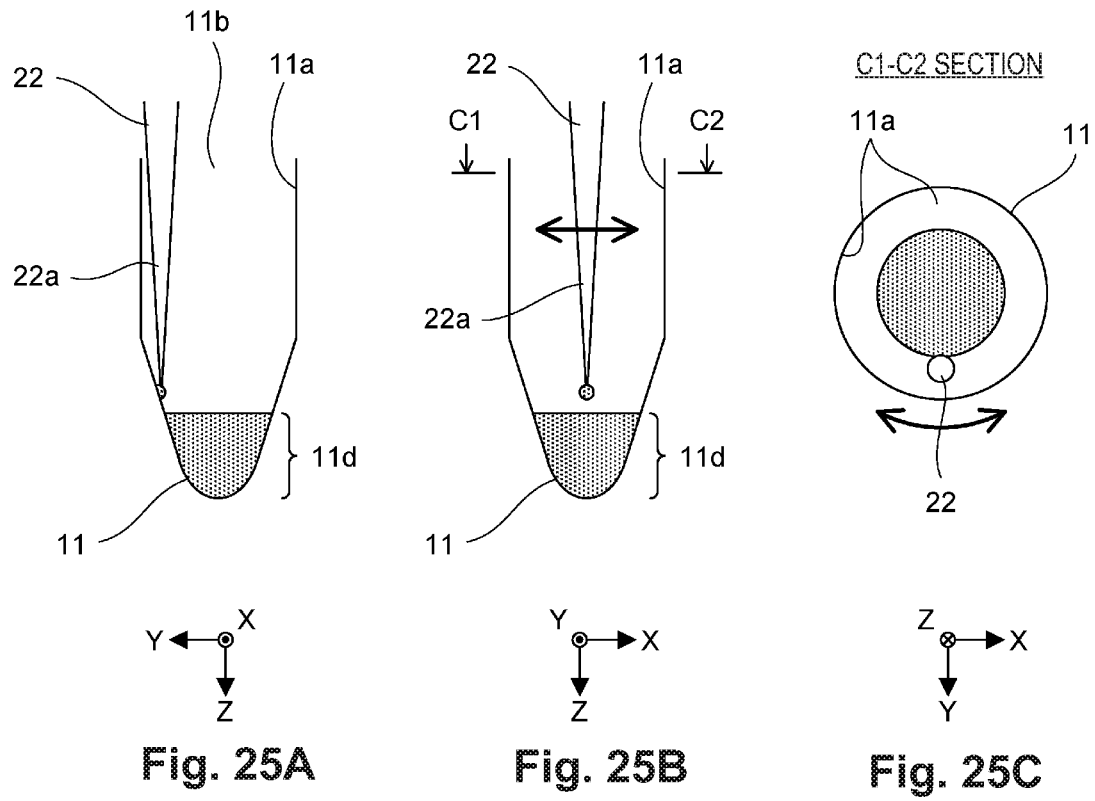
FIGS. 25A to 25C are side and sectional views of a container illustrating a given state in a droplet collecting step according to Embodiment 2.

When the elution liquid is thus discharged from a lower position in the mixing step, droplets containing magnetic particles attach to a lower position on the inner wall 11a of the container 11 than in Embodiment 1, as illustrated in FIG. 24D to 24F. Thus, in Embodiment 2, in Step S5 of FIG. 1, as illustrated in FIGS. 25A to 25C, the pipette tip 22 is moved circumferentially as in Embodiment 1, with the tip of the pipette tip 22 touching a lower position on the inner wall 11a. Then, the moving step is performed in Step S6 of FIG. 1.

Figure 25D:
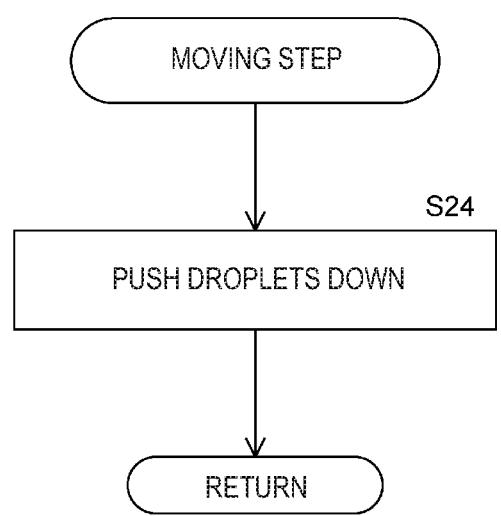
FIG. 25D is a flowchart illustrating a moving step according to Embodiment 2.

The moving step in Embodiment 2 is constructed as illustrated in FIG. 25D. The moving step illustrated in FIG. 25D does not have Steps S21 to S23 and S25 in the moving step in Embodiment 1 illustrated in FIG. 2B. In Embodiment 2, in Step S24, the pipette tip 22 is lowered to push down droplets. In this event, the tip of the pipette tip 22 is lowered to the liquid level of the elution liquid accumulated in the accumulation area 11d. Thereby, the droplets collected as illustrated in FIGS. 25A to 25C are moved to the accumulation area 11d. The rest of the processing in Embodiment 2 is the same as that in Embodiment 1.

In Embodiment 2, the elution liquid is discharged toward the attachment area 11c from a lower position in the mixing step, and therefore droplets attached to the inner wall 11a are distributed at positions near the accumulation area 11d. Thus, the moving step does not need to perform the operation of moving the pipette tip 22 away from the inner wall, elevating the pipette tip 22, and moving the pipette tip 22 close to the inner wall, like Embodiment 1. Thus, Embodiment 2 not only can prevent droplets containing magnetic particles from remaining on the inner wall 11a of the container 11 but also can simplify the control of the pipette tip 22 compared to Embodiment 1.

Embodiment 3

In Embodiment 1, after the sample reacts with the reagent in the container 12, the specimen is dispensed from the container 12 to the container 11, and cleaning and DNA releasing are performed in the container 11. However, one or more embodiments are not limited to this, and the processing cartridge 10 may be provided with a separate container for the cleaning so that the cleaning and the DNA releasing may be conducted in different containers.

Figure 26A:
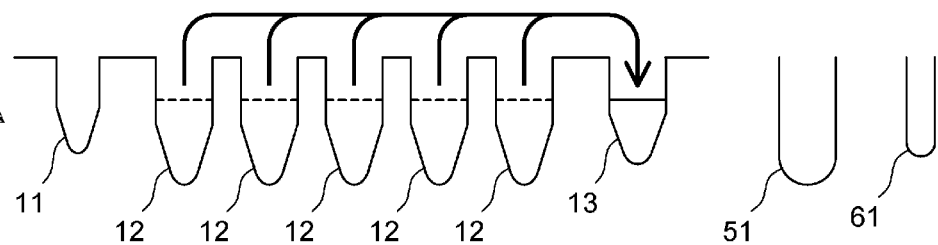
FIGS. 26A to 26F are diagrams illustrating a procedure of the processing performed by a sample processing apparatus according to Embodiment 3.

As illustrated in FIG. 26A, the processing cartridge 10 of Embodiment 3 further includes a container 13 for cleaning, compared to Embodiment 1. The container 13 of Embodiment 3 has the same size as the container 11 of Embodiment 1. The container 11 of Embodiment 3 is smaller than the container 11 of Embodiment 1 to accord with the liquid amount of elution liquid. Further, Embodiment 3 is provided with a configuration for applying magnetic force to the container 13 when the processing cartridge 10 is set in the sample processing apparatus 100. This configuration is the same as that of the magnetic force application part 420 illustrated in FIG. 14.

The rest of the configuration of Embodiment 3 is the same as that of Embodiment 1. The controller 601 of Embodiment 3 performs control as follows. Descriptions are given below for controls different from Embodiment 1.

In Embodiment 3, after a sample reacts with reagent in each of five containers 12, the container 13 is used instead of the container 11 for the processing of Steps S201 to S205. In this processing, as illustrated in FIG. 26A, a predetermined quantity of specimens is dispensed from each container 12 to the container 13 sequentially, and impurities contained in the specimen in the container 13 are removed as a liquid component.

Figure 26B:
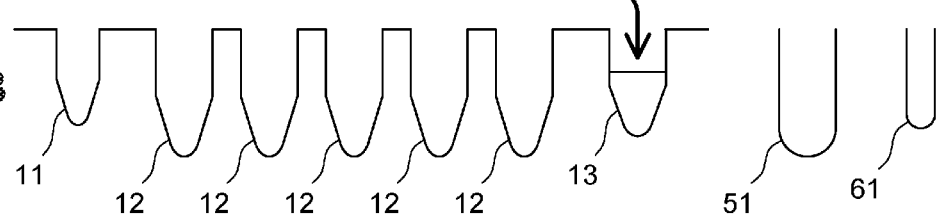

Next, the processing of Steps S301 to S310 is performed using the container 13 in place of the container 11. In this processing, as illustrated in FIG. 26B, the first and second cleaning liquids are dispensed to the container 13, and impurities contained in the specimen in the container 13 are removed as a liquid component. Next, the processing of Steps S401 and S402 is performed using the container 13 in place of the container 11. In this processing, as illustrated in FIG. 26B, the third cleaning liquid is dispensed to the container 13, and the specimen in the container 13 is agitated.

Figure 26C:
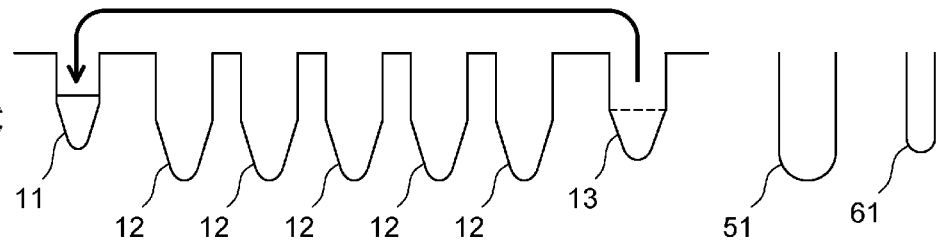
Figure 26D:
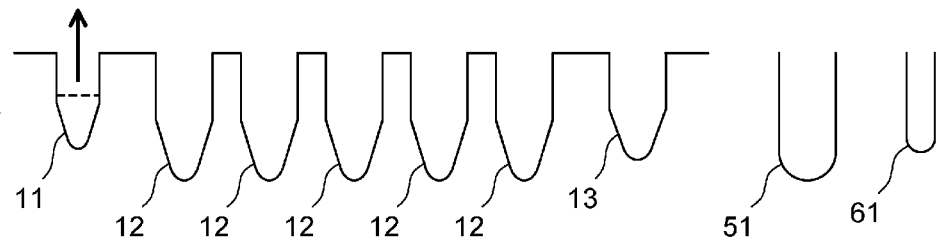

Next, as in Embodiment 1, the magnet 104 is moved close to the container 11 in Step S403. Next, in Embodiment 3, after the processing of Step S403, the specimen in the container 13 is dispensed to the container 11 as illustrated in FIG. 26C. Then, as in Embodiment 1, the liquid component in the container 11 is removed in Step S404, as illustrated in FIG. 26D. In this event, as in Embodiment 1, magnetic particles are caused to adhere to the inner wall 11a of the container 11.

Figure 26E:
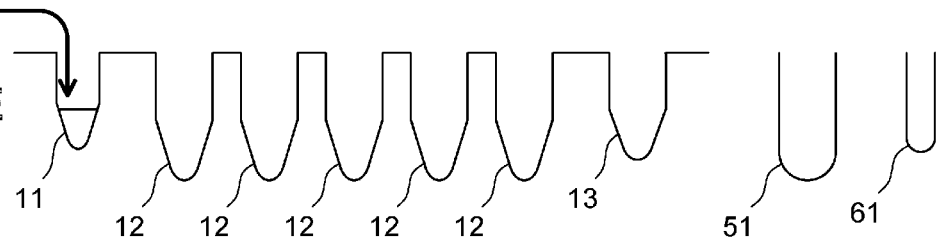
Figure 26F:
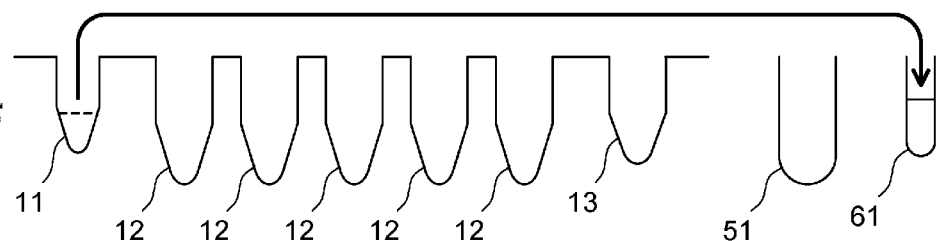
Figure 27:
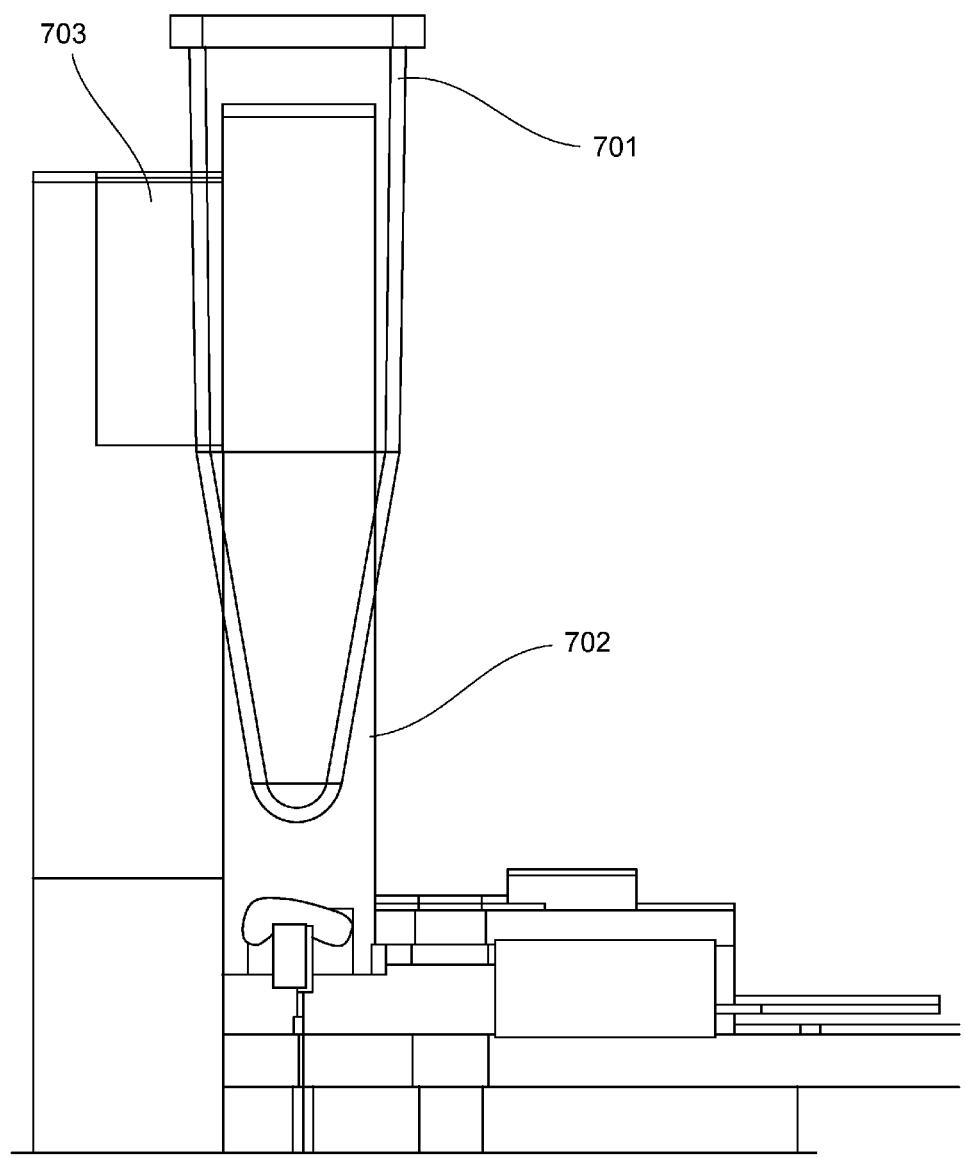
FIG. 27 is a schematic diagram illustrating a configuration of a related art.

Thereafter, as in Embodiment 1, the processing of Steps S405 to S412 is performed. In the mixing step in Step S406, elution liquid is dispensed to the container 11 as illustrated in FIG. 26E. In the mixing step, the magnetic particles attached to the inner wall 11a on the Y-axis positive side are detached by the elution liquid. In Step S407, droplets attached to the inner wall 11a are collected. In the moving step in Step S408, the collected droplets are moved to the accumulation area 11d. In Step S411, the liquid in the container 11 is dispensed to the container 61 as illustrated in FIG. 26F.

Since the container 11 in Embodiment 3 is smaller than that of Embodiment 1, Embodiment 3 can hinder magnetic particles from staying in the bottom portion of the container 11 and ensure that the magnetic particles adhere to the part of the inner wall 11a that faces the magnet. Thereby, removal of the liquid component in Step S404 and taking out of the liquid in Step S411 can be performed surely.

The invention includes other embodiments in addition to the above-described embodiments without departing from the spirit of the invention. The embodiments are to be considered in all respects as illustrative, and not restrictive. The scope of the invention is indicated by the appended claims rather than by the foregoing description. Hence, all configurations including the meaning and range within equivalent arrangements of the claims are intended to be embraced in the invention.

The invention claimed is:
1. A sample processing method comprising:
removing a liquid component in a container housing a suspension containing a magnetic particle bound with an analyte, while causing magnetic adhesion of the magnetic particle in the container;
discharging an elution liquid for releasing the analyte from the magnetic particle from a pipette into the container from which the liquid component has been removed so as to mix the magnetic particle and the elution liquid together;
moving, after discharging the elution liquid from the pipette into the container, the pipette relative to and close to an inner wall of the container so as to collect a droplet attached to the inner wall onto an outer surface of the pipette; and moving a tip of the pipette to an accumulation area in which the elution liquid accumulates in the container so as to move the droplet collected on the outer surface of the pipette to the accumulation area.

2. The sample processing method according to claim 1, wherein moving the tip of the pipette to the accumulation area in the container comprises:
moving the pipette away from the inner wall;
elevating the pipette;
moving the pipette close to the inner wall; and
lowering the pipette to push down the droplet.

3. The sample processing method according to claim 2, wherein moving the tip of the pipette to the accumulation area comprises performing the moving the tip of the pipette as recited in claim 2 a plurality of times.

4. The sample processing method according to claim 1, wherein moving the tip of the pipette to the accumulation area comprises moving the tip of the pipette at least to a liquid level of the elution liquid accumulated in the accumulation area.

5. The sample processing method according to claim 1, wherein moving the pipette relative to and close to the inner wall of the container comprises bringing the pipette into contact with the inner wall of the container.

6. The sample processing method according to claim 1, wherein the pipette comprises a nozzle and a pipette tip attached to the nozzle.

7. The sample processing method according to claim 6, wherein moving the pipette relative to and close to the inner wall of the container comprises moving the nozzle, to which the pipette tip is attached, in a direction orthogonal to a center axis of the container with the pipette tip touching the inner wall of the container.

8. The sample processing method according to claim 6, wherein moving the pipette relative to and close to the inner wall of the container comprises moving the nozzle, to which the pipette tip is attached, circumferentially along the inner wall of the container.

9. The sample processing method according to claim 1, wherein discharging the elution liquid from the pipette into the container comprises discharging the elution liquid from the pipette into the container after cancelling application of a magnetic force causing the magnetic adhesion of the magnetic particle in the container.

10. The sample processing method according to claim 1, wherein discharging the elution liquid from the pipette into the container comprises discharging the elution liquid from the pipette to an attachment area of the inner wall of the container on which the magnetic particle is attached.

11. The sample processing method according to claim 10, wherein discharging the elution liquid from the pipette into the container comprises:
aspirating the elution liquid accumulated in the accumulation area into the pipette; and
discharging the aspirated elution liquid to the attachment area.

12. The sample processing method according to claim 11, wherein discharging the elution liquid from the pipette into the container comprises performing the discharging the elution liquid from the pipette into the container as recited in claim 11 a plurality of times.

13. The sample processing method according to claim 11, wherein discharging the elution liquid from the pipette into the container comprises discharging, after discharging the aspirated elution liquid to the attachment area, another elution liquid that contains no magnetic particle to the attachment area.

14. The sample processing method according to claim 1, wherein discharging the elution liquid from the pipette into the container comprises discharging the elution liquid from the pipette into the container along the inner wall of the container.

15. The sample processing method according to claim 1, further comprising:
supplying, before removing the liquid component from the container, the suspension into the container, wherein
a liquid amount of the elution liquid discharged into the container is less than a liquid amount of the suspension supplied into the container.

16. The sample processing method according to claim 1, wherein a magnetic force causing the magnetic adhesion of the magnetic particle in the container is applied from a side of the container.

17. The sample processing method according to claim 16, wherein the magnetic force is applied to at least an area of the container which is larger than the accumulation area.

18. The sample processing method according to claim 1, further comprising:
aspirating, after moving the tip of the pipette to the accumulation area in the container, liquid containing the analyte from the container, while causing magnetic adhesion of the magnetic particle in the container.

19. The sample processing method according to claim 1, wherein the analyte comprises a nucleic acid.

20. The sample processing method according to claim 19, wherein the nucleic acid comprises cell-free DNA.

21. A sample processing method comprising:
removing a liquid component in a container housing a first liquid containing a magnetic particle bound with an analyte, while causing magnetic adhesion of the magnetic particle in the container;
discharging a second liquid, which is different from the first liquid, from a pipette into the container from which the liquid component has been removed so as to mix the magnetic particle and the second liquid together;
moving, after discharging the elution liquid from the pipette into the container, the pipette relative to and close to an inner wall of the container so as to collect a droplet attached to the inner wall onto an outer surface of the pipette; and
moving a tip of the pipette to an accumulation area in which the second liquid accumulates in the container so as to move the droplet collected on the outer surface of the pipette to the accumulation area.

22. A sample processing apparatus comprising:
a dispensing part that comprises a pipette and is configured to dispense a liquid via the pipette into a container;
a magnetic force application part that comprises a magnet and is configured to apply a magnetic force to the container; and
a controller, wherein:
the controller causes the dispensing part to remove a liquid component in a container housing a suspension containing a magnetic particle bound with an analyte in a condition in which the controller causes the magnetic force application part to apply the magnetic force to the container and cause magnetic adhesion of the magnetic particle in the container;
the controller causes the dispensing part to discharge an elution liquid for releasing the analyte from the magnetic particle via the pipette into the container from which the liquid component has been removed;

after the dispensing part discharges the elution liquid into the container, the controller causes the pipette to move close to an inner wall of the container to collect a droplet attached to the inner wall onto an outer surface of the pipette; and the controller causes the pipette to move to an accumulation area in which the elution liquid accumulates in the container to move the droplet collected on the outer surface of the pipette to the accumulation area.

23. A sample processing method comprising:

removing a liquid component in a container housing a suspension containing a magnetic particle bound with an analyte, while causing magnetic adhesion of the magnetic particle in the container;

discharging, from a pipette to an attachment area of the inner wall of the container, an elution liquid for releasing the analyte from the magnetic particle, wherein the magnetic particle is attached on the attachment area of the inner wall of the container from which the liquid component has been removed; and performing, a plurality of times, an operation comprising:

aspirating the elution liquid discharged and accumulated in the container; and discharging the aspirated elution liquid to the attachment area of the inner wall of the container on which the magnetic particle is attached.

24. A sample processing apparatus comprising:

a dispensing part that comprises a pipette and is configured to dispense a liquid via the pipette into a container;

a magnetic force application part that comprises a magnet and is configured to apply a magnetic force to the container; and a controller, wherein:

the controller causes the dispensing part to remove a liquid component in a container housing a suspension containing a magnetic particle bound with an analyte in a condition in which the controller causes the magnetic force application part to apply the magnetic force to the container and cause magnetic adhesion of the magnetic particle in the container;

the controller causes the dispensing part to discharge an elution liquid for releasing the analyte from the magnetic particle via the pipette to an attachment area of the inner wall of the container, wherein the magnetic particle is attached on the attachment area of the inner wall of the container from which the liquid component has been removed; and the controller causes the dispensing part to perform, a plurality of times, an operation comprising: aspirating the elution liquid discharged and accumulated in the container; and discharging the aspirated elution liquid to the attachment area of the inner wall of the container.

* * * * *